(12) United States Patent
Take et al.

(10) Patent No.: US 9,688,674 B2
(45) Date of Patent: Jun. 27, 2017

(54) SELECTIVE EP4 RECEPTOR ANTAGONISTIC SUBSTANCE FOR TREATMENT OF CANCER

(71) Applicant: RaQualia Pharma Inc., Aichi (JP)

(72) Inventors: Yukinori Take, Aichi (JP); Shinichi Koizumi, Aichi (JP); Takako Okumura, Aichi (JP); Kazuhiko Nonomura, Aichi (JP)

(73) Assignee: AskAt Inc., Nagoya (JP)

( * ) Notice: Subject to any disclaimer, the term of this patent is extended or adjusted under 35 U.S.C. 154(b) by 82 days.

(21) Appl. No.: 14/547,247

(22) Filed: Nov. 19, 2014

(65) Prior Publication Data

US 2015/0111920 A1   Apr. 23, 2015

Related U.S. Application Data

(63) Continuation of application No. 13/265,216, filed as application No. PCT/JP2010/057114 on Apr. 22, 2010, now Pat. No. 8,921,391.

(30) Foreign Application Priority Data

Apr. 22, 2009 (JP) ................ 2009-104568
Jan. 27, 2010 (JP) ................ 2010-015445

(51) Int. Cl.
*A61K 31/192* (2006.01)
*A61K 31/437* (2006.01)
(Continued)

(52) U.S. Cl.
CPC .......... *C07D 471/04* (2013.01); *A61K 31/192* (2013.01); *A61K 31/437* (2013.01);
(Continued)

(58) Field of Classification Search
CPC .... A61K 31/192; A61K 31/437; A61K 31/44; A61K 31/4412; A61K 45/06; C07C 235/60; C07D 213/82; C07D 471/04
See application file for complete search history.

(56) References Cited

U.S. PATENT DOCUMENTS 6,710,054 B2   3/2004   Nakao et al.
6,710,205 B2   3/2004   Tani et al.
(Continued)

FOREIGN PATENT DOCUMENTS

JP   2004-517054   6/2004
JP   2007-504210   3/2007
(Continued)

OTHER PUBLICATIONS

Sung et al. "Lack of Expression of the EP2 but not EP3 Receptor for Prostaglandin E2 Results in Suppression of Skin Tumor Development" Cancer Res, 2005, vol. 65, No. 20, pp. 9304-9311.*
Akio Murase et al., "In vitro pharmacological characterization of CJ-042794, a novel, potent, and selective prostaglandin EP4 receptor antagonist", Life Sciences, Jan. 16, 2008, vol. 82, No. 3-4, pp. 226-232.
Koji Takeuchi et al., "Effect of (S)-4-(1-(5-Chloro-2-(4-flurophertyoxy)benzamido)ethyl) Benzoic Acid (CJ-42794), a Selective Antagonist of Prostaglandin E Receptor Subtype 4, on Ulcerogenic and Healing Responses in Rat Gastrointestinal Mucosa", The Journal of Pharmacology and Experimental Therapeutics, Sep. 1, 2007, vol. 322, No. 3, pp. 903-912.
(Continued)

*Primary Examiner* — Kendra D Carter
(74) *Attorney, Agent, or Firm* — Wenderoth, Lind & Ponack, L.L.P.

(57) ABSTRACT

This invention provides a medicament for the treatment of cancer, which cause a reduction of cancer. This invention relates to use of a compound which has inhibitory activities against prostaglandin E2 receptor (EP4 receptor) and is represented by the following general formula (I), (II), (III), or (IV), or a pharmaceutically acceptable salt thereof, or a pharmaceutical composition comprising the compound or the salt for the manufacture of a medicament for the treatment of cancer. The invention relates to a method for treatment of cancer comprising administering the compound or a pharmaceutically acceptable salt thereof, or a pharmaceutical composition comprising the compound or the salt to humans or animals. The compound or a pharmaceutically acceptable salt thereof, or the pharmaceutical composition may be used in combination with one or more second active agents.

(I)

(II)

(III)

(Continued)

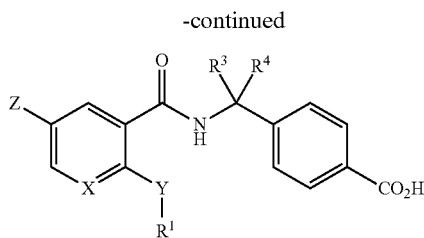

(IV)

6 Claims, 4 Drawing Sheets

(51) Int. Cl.
*A61K 31/44* (2006.01)
*A61K 31/4412* (2006.01)
*A61K 45/06* (2006.01)
*C07C 235/60* (2006.01)
*C07D 213/82* (2006.01)
*C07D 471/04* (2006.01)

(52) U.S. Cl.
CPC .......... *A61K 31/44* (2013.01); *A61K 31/4412* (2013.01); *A61K 45/06* (2013.01); *C07C 235/60* (2013.01); *C07D 213/82* (2013.01)

(56) References Cited

U.S. PATENT DOCUMENTS

| | | |
|---|---|---|
| 6,861,441 B1 | 3/2005 | Clayton et al. |
| 7,141,580 B2 | 11/2006 | Nakao et al. |
| 7,196,198 B2 | 3/2007 | Tani et al. |
| 7,238,714 B2 | 7/2007 | Nakao et al. |
| 7,479,564 B2 | 1/2009 | Nakao et al. |
| 7,534,914 B2 | 5/2009 | Koike et al. |
| 2002/0107273 A1 | 8/2002 | Nakao et al. |
| 2003/0114435 A1 | 6/2003 | Tani et al. |
| 2003/0220372 A1 | 11/2003 | Hirano et al. |
| 2004/0127487 A1 | 7/2004 | Tani et al. |
| 2004/0181059 A1 | 9/2004 | Nakao et al. |
| 2005/0065188 A1 | 3/2005 | Nakao et al. |
| 2005/0250818 A1 | 11/2005 | Koike et al. |
| 2005/0267170 A1 | 12/2005 | Koike et al. |
| 2007/0155732 A1 | 7/2007 | Nakao et al. |
| 2009/0018158 A1 | 1/2009 | Haruta et al. |
| 2009/0099226 A1 | 4/2009 | Belley et al. |
| 2009/0163558 A1 | 6/2009 | Koike et al. |

FOREIGN PATENT DOCUMENTS

| | | |
|---|---|---|
| JP | 2007-536366 | 12/2007 |
| JP | 2007-536367 | 12/2007 |
| JP | 2008-540584 | 11/2008 |
| WO | 01/10426 | 2/2001 |
| WO | 01/62708 | 8/2001 |
| WO | 02/32900 | 4/2002 |
| WO | 03/086390 | 10/2003 |
| WO | 03/086391 | 10/2003 |
| WO | 2005/021508 | 3/2005 |
| WO | 2005/102389 | 11/2005 |
| WO | 2005/105732 | 11/2005 |
| WO | 2006/095268 | 9/2006 |

OTHER PUBLICATIONS

Extended European Search Report issued Nov. 27, 2015 in corresponding European Patent Application No. 15182580.9.
International Search Report issued May 25, 2010 in International (PCT) Application No. PCT/JP2010/057114.
D. P. Cherukuri et al., "The EP4 Receptor Antagonist, L-161,982, Blocks Prostaglandin E2-Induced Signal Transduction and Cell Proliferation in HCA7 Colon Cancer Cells", Experimental Cell Research, vol. 313, No. 14, pp. 2969-2979, 2007.
X. Mia et al., "Prostaglandin E Receptor EP4 Antagonism Inhibits Breast Cancer Metastasis", Cancer Research, vol. 66, No. 6, pp. 2923-2927, 2006.
T. Kitamura et al., "Combined Effects of Prostaglandin E Receptor Subtype $EP_1$, and Subtype EP4 Antagonists on Intestinal Tumorigenesis in *Adenomatous Polyposis coli* Gene Knockout Mice", Cancer Science, vol. 94, No. 7, pp. 618-621, Jul. 2003.
English translation of International Preliminary Report on Patentability and Written Opinion dated Nov. 22, 2011 for PCT/JP2010/057114.
Supplementary European Search Report issued May 17, 2013 in corresponding European Application No. 10 76 7106.7.
Yang et al., "Host and Direct Antitumor Effect and Profound Reduction in Tumor Metastasis with Selective EP4 Receptor Antagonism", Cancer Research, vol. 66, No. 19, Oct. 1, 2006, pp. 9665-9672.
Murase et al., "Characterization of Binding Affinity of CJ-023,423 for Human Prostanoid EP4 Receptor", Pharmacology, vol. 82, No. 1, 2008, pp. 10-14.
Wang et al. "Prostaglandin E2 induces Vascular Endothelial Growth Factor Secretion in Prostrate Cancer Cells Through EP2 Receptor-Mediated cAMP Pathway", Molecular Carcinogenesis, 2007, vol. 46, pp. 912-923.
Han et al. "Suppression of prostaglandin E2 receptor subtype EP2 by PPARgamma ligands inhibits human lung carcinoma cell growth", Biochemical and Biophysical Research Communications, 2004, vol. 314, pp. 1093-1099.
J. G. Cannon Chapter Nineteen in Burger's Medicinal Chemistry and Drug Discovery, Fifth Edition, vol. I: Principles and Practice, Wiley-Interscience, 1995, pp. 783-802, 784.
Wu et al. "A human colonic commensal promotes colon tumorigenesis via activation of T helper type 17 T cell responses", Nature Medicine, Sep. 2009, vol. 15, No. 9, pp. 1016-1023.
Sinha et al. "Prostaglandin E2 Promotes Tumor Progression by Inducing Myeloid-Derived Suppressor Cells", Cancer Res, May 2007, vol. 67, No. 9, pp. 4507-4513.
Sheridan, R.P. "The Most Common Chemical Replacements in Drug-Like Compounds", J. Chem. Inf. Comput., 2002, vol. 42, pp. 103-108.
Chell et al. "EP4 Receptor Expression and Colorectal Carcinogenesis", Cancer Research, 2006, vol. 66, No. 6, pp. 3106-3113.
Timoshenko et al. "Role of prostaglandin E2 receptors in migration of murine and human breast cancer cells", Experimental Cell Research, 2003, vol. 289, pp. 265-274.

* cited by examiner

SELECTIVE EP4 RECEPTOR ANTAGONISTIC SUBSTANCE FOR TREATMENT OF CANCER

This application is a continuation application of U.S. application Ser. No. 13/265,216, which issued as U.S. Pat. No. 8,921,391 on Dec. 30, 2014, which is a U.S. national stage application of International Application No. PCT/JP2010/057114, filed Apr. 22, 2010.

TECHNICAL FIELD

This invention relates to use of a compound which has inhibitory activities against prostaglandin E2 receptor (EP4 receptor) and is represented by the following general formula (I), (II), (III), or (IV), or a pharmaceutically acceptable salt thereof (hereafter it is sometimes called the compound of the present invention), or a pharmaceutical composition comprising the compound or the salt for the manufacture of a medicament for the treatment of cancer. The invention relates to a method for the treatment of cancer comprising administering the compound of the present invention or a pharmaceutical composition comprising the same to humans or animals. Further, this invention relates to a pharmaceutical composition or a kit comprising the compound of the present invention or a pharmaceutically acceptable salt thereof.

BACKGROUND ART

Prostaglandins are mediators associated with various symptoms such as pain, fever and inflammation. Especially, prostaglandin E2 (PGE2) is a predominant eicosanoid detected in inflammation conditions. In addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis, cancer invasion and metastasis, and the like.

There are four receptor subtypes, EP1, EP2, EP3 and EP4, which display different pharmacological properties. EP4 receptor belongs to a G protein coupled receptor subfamily, is known as a receptor with seven transmembrane, and plays a significant role for biological events which PGE2 relates to by stimulating cAMP production. From the aspect of pharmacological studies, investigation of compounds with EP4 receptor antagonistic activities has been conducted and selective antagonists have also been known.

PGE2 is a predominant eicosanoid detected in inflammation conditions, and in addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis, cancer metastasis, and the like. Non-patent literature 1 to 3 disclose the character of the prostanoid receptors, relationship thereof with therapy, and selective agonists and antagonists most generally used therefor.

On the other hand, it is reported that PGE2 is highly expressed in the cancer tissue in the different types of cancer, and it is also clarified that PGE2 relates to the development of cancer and disease condition. It is known that PGE2 relates to activation of cell proliferation and inhibition of cell death (apoptosis) and plays an important role in the process of cancer progression and metastasis. But because of a lot of reports varying depending on the difference of statuses such as cancer type, progress process and the like, at this time point, the medical consensus has never obtained on which PGE receptor mediates these various functions of PGE2 associated with cancers.

Regarding the relation between EP4 and cancer, at the cellular level, a report (non-patent literature 4) which shows growth inhibition of the colon cancer cell (HCA-7) by an EP4 receptor antagonist, L-161,982, has been found. Regarding metastasis of cancer, a report (non-patent literature 5) which shows metastasis suppression of breast cancer cells by an EP4 receptor antagonist, AH23848 or ONO-AE3-208, and the like have been found.

Meanwhile, regarding the experiments using animals, it has been reported that an EP4 receptor antagonist, ONO-AE2-227 shows reduced formation of azoxymethane-induced colon aberrant crypt foci and reduced formation of intestinal polyp in APC gene knockout mice (non-patent literature 6).

As stated above, it is known that EP4 relates to development, growth and metastasis of cancer, and in addition, reports which suggest prevention, growth inhibition, and metastasis suppression of cancer by EP4 receptor antagonists are also recognized. But the basis of cancer chemotherapy is "to shrink cancer tissues which have already been formed" and examples of EP4 receptor antagonists which show shrinkage of cancer tissues already formed in animal organs have never been known, and there has been a real need for such compounds.

CITATION LIST

Non-Patent Literature

Non-patent Literature 1: Eicosanoids: From Biotechnology to Therapeutic Applications, Folco, Samuelsson, Maclouf and Velo eds, Plenum Press, New York, 1996, chapter 14, p. 137-154

Non-patent Literature 2: Journal of Lipid Mediators and Cell Signalling, 14: 83-87 (1996)

Non-patent Literature 3: Prostaglandins and Other Lipid Mediators, 69: 557-573 (2002)

Non-patent Literature 4: Experimental Cell Research Volume 313, Issue 14, 15 Aug. 2007, Pages 2969-2979

Non-patent Literature 5: Cancer Research, Volume 66, Issue 6, Mar. 15, 2006

Non-patent Literature 6: Cancer Science Volume 94, Issue 7, 1 Jul. 2003, Pages 618-621; Cancer Research Volume 62, Issue 1, 1 Jan. 2002, Pages 28-32

SUMMARY OF INVENTION

Technical Problem

The purpose of this invention is to provide a medicament for the treatment of cancer in order to shrink cancer tissues.

Solution to Problem

After inventors of this invention conducted intensive research in order to solve the said problem above, the inventors discovered that a compound of formula (I), (II), (III), or (IV) or a pharmaceutically acceptable salt thereof was dramatically able to shrink cancer tissues which were formed in animal cancer models and then completed the present invention.

Namely, the present invention is based on the finding that the compounds of the present invention with EP4 selective antagonistic activity shrank tumor mass when determining the effects of the EP4 selective antagonists on the mouse spontaneous gastric cancer model (K19-Wnt1/C2mE mice, Gastroenterology Volume 131, Pages 1086-1095, 2006). This gastric cancer model involves PGE2-mediated mechanism of tumor progression, and the above findings revealed first in the world that the compounds of the invention have been proved effective in shrinking PGE2-mediated tumor tissues. In addition, the compounds of the present invention also showed the effects in the model of gastroenterological cancer, prostate cancer, lung cancer, and breast cancer.

Advantageous Effects of Invention

Therefore, the compound of this invention is useful for patients who are required to receive treatment for cancer which PGE2 relates to. "Cancer which PGE2 relates to" includes brain tumor, bone cancer, neoplasm derived from epithelial cells (epithelial cancer), for example, basal cell carcinoma, adenocarcinoma, gastroenterological cancer (e.g. lip cancer, oral cancer, esophageal cancer, intestinal cancer, colon cancer and gastric cancer), liver cancer, bladder cancer, pancreatic cancer, ovarian cancer, cervical cancer, lung cancer, breast cancer, skin cancer (e.g. squamous cell and basal cell carcinoma), prostate cancer, renal cell carcinoma, and other known cancers which affect the epithelial cells in the body. Cancer is preferably selected from gastroenterological cancer, prostate cancer, lung cancer, and breast cancer.

DESCRIPTION OF EMBODIMENTS

Figure 1:
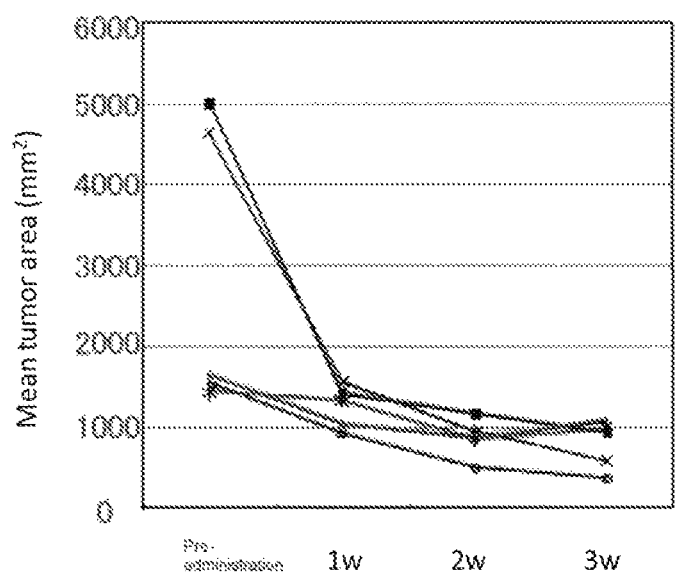
FIG. 1 shows change of mean tumor area of cross section in gastric tumor measured by X-ray CT scan.

Compounds of the present invention which are useful for treatment of cancer are compounds of formula (I), (II), (III), or (IV), or pharmaceutically acceptable salts thereof. Compounds of the present invention include the solvates, complexes, polymorphs, prodrugs, isomers, and isotope-labeled compounds.

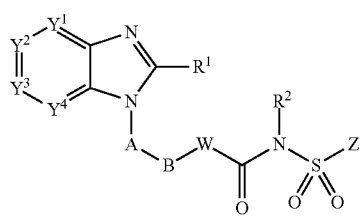

(I)

(wherein
$Y^1$, $Y^2$, $Y^3$ and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)$_m$—, $Q^1$-, pyrrolidinyl, piperidyl, oxopyrrolidinyl, oxopiperidyl, amino, mono- or di-($C_{1-8}$ alkyl)amino, $C_{1-8}$alkylC(=O)—N($R^3$)— or $C_{1-8}$alkyl-S(O)$_m$—N($R^3$)—; wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)$_m$—, $C_{3-7}$ cycloalkyl-, cyano, indanyl, 1,2,3,4-tetrahydronaphthyl, 1,2-dihydronaphthyl, pyrrolidinyl, piperidyl, oxopyrrolidinyl, oxopiperidyl, $Q^1$-, $Q^1$-C(=O)—, $Q^1$-O—, $Q^1$-S(O)$_m$—, $Q^1$-C$_{1-4}$alkyl-O—, $Q^1$-C$_{1-4}$alkyl-S(O)$_m$—, $Q^1$-C$_{1-4}$alkyl-C(O)—N($R^3$)—, $Q^1$-C$_{1-4}$alkyl-N($R^3$)— or $C_{1-4}$alkyl-C(O)—N($R^3$);

$Q^1$ is a 5- to 12-membered monocyclic or bicyclic aromatic ring optionally containing up to 4 heteroatoms selected from O, N and S, and being optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$alkylC(=O)—, HO(O=)C—, $C_{1-4}$ alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or NH$_2$(HN=)C—;

A is a 5- to 6-membered monocyclic aromatic ring optionally containing up to 3 heteroatoms selected from O, N and S, wherein said 5- to 6-membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, acetyl, $R^3$N($R^4$)C(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)— and NH$_2$(HN=)C—;

B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene, $C_{1-2}$ alkylene-O—$C_{1-2}$ alkylene or $C_{1-6}$ alkylene optionally substituted with an oxo group or $C_{1-3}$ alkyl;

W is NH, N—$C_{1-4}$ alkyl, O, S, N—OR$^5$ or a covalent bond;

$R^2$ is H, $C_{1-4}$ alkyl, OH or $C_{1-4}$ alkoxy;

Z is a 5- to 12-membered monocyclic or bicyclic aromatic ring optionally containing up to 3 heteroatoms selected from O, N and S, wherein said 5- to 12-membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C—, $C_{1-4}$ alkylsulfonylamino, $C_{3-7}$ cycloalkyl, NH$_2$(HN=)C—, $Q^2$-S(O)$_m$—, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$alkylC(=O)—, HO(O=)C—, $C_{1-4}$alkyl-O(O=)C—, $C_{1-4}$ alkylsulfonylamino, $C_{3-7}$ cycloalkyl, $R^3$C(=O)N($R^4$)—, NH$_2$(HN=)C—, $R^3$N($R^4$)C(=O)—, $R^3$N($R^4$)S(O)$_m$—, $Q^2$-, $Q^2$-C(=O)—, $Q^2$-O—, or $Q^2$-$C_{1-4}$ alkyl-O—, or two adjacent L groups are optionally joined together to form an alkylene chain having 3 or 4 members in which one or two (nonadjacent) carbon atoms are optionally replaced by oxygen atom(s);

m is 0, 1 or 2;

$R^3$ and $R^4$ are independently selected from H and $C_{1-4}$ alkyl;

$R^5$ is H, $C_{1-4}$ alkyl, $C_{1-4}$ alkyl-(O=)C— or $C_{1-4}$ alkyl-O—(O=)C—; and $Q^2$ is a 5- to 12-membered monocyclic or bicyclic aromatic ring, or a 5- to 12-membered tricyclic ring optionally containing up to 3 heteroatoms selected from O, N and S, wherein said 5- to 12-membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxyl, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or $NH_2(HN=)C$—; or when formula (I) includes OH and/or $CO_2H$, said OH and —COOH may be independently esterified to form a pharmaceutically acceptable ester);

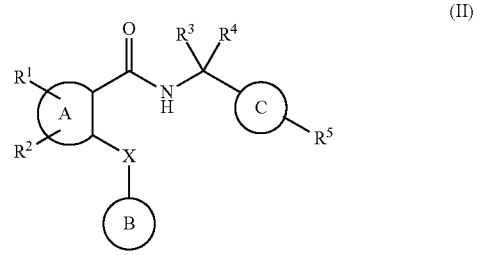

(II)

(wherein ring A represents a phenyl group or a pyridyl group ring B represents an aryl group or a heteroaryl group;

ring C represents a 1,4-phenylene group;

$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an amino carbonyl group;

$R^3$ and $R^4$ independently represent a hydrogen atom or an alkyl group having from 1 to 4 carbon atoms; or $R^3$ and $R^4$ groups may be joined together to form an alkylene chain having 2 to 6 carbon atoms;

$R^5$ represents $CO_2H$, $CO_2W$,

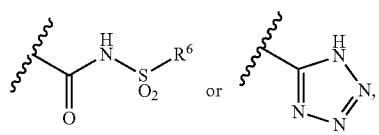

$R^6$ represents an alkyl group having 1 to 6 carbon atoms, a cycloalkyl group having from 3 to 7 ring atoms, an aryl group or a heteroaryl group;

X represents a methylene group, an oxygen atom or a sulfur atom;

said aryl group has from 6 to 10 carbon atoms;

said heteroaryl group is a 5- to 10-membered aromatic heterocyclic group containing from 1 to 3 heteroatoms selected from the group consisting of a sulfur atom, an oxygen atom and a nitrogen atom;

said aryl group and said heteroaryl group referred to in the definition of ring B are unsubstituted or are substituted by at least one substituent selected from the group consisting of substituents alpha;

said 1,4-phenylene group referred to in the definition of ring C is unsubstituted or is substituted by at least one substituent selected from the group consisting of substituents beta;

said aryl group and said heteroaryl group referred to in the definitions of $R^6$ and alpha are unsubstituted or are substituted by at least one substituent selected from the group consisting of substituents beta;

said substituents alpha are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, aminocarbonyl groups, alkenyl groups having from 2 to 5 carbon atoms, alkylthio groups having from 1 to 4 carbon atoms, aminosulfinyl groups, aminosulfonyl groups, hydroxyl groups, hydroxyalkyl groups having from 1 to 4 carbon atoms, nitro groups, amino groups, carboxy groups, alkoxycarbonyl groups having 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms each in both the alkanoyl and alkyl parts, alkanoyl(alkyl)aminoalkyl groups having from 1 to 6 carbon atoms each in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms; or two adjacent alpha groups may be joined together to form an alkylene or alkenylene chain having 3 or 4 carbon atoms;

said substituents beta are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups; and W is a pharmaceutically acceptable ester pro-drug group);

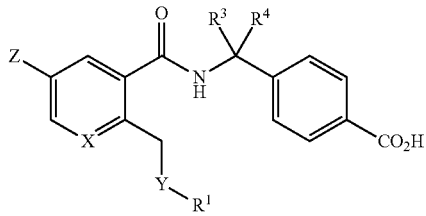

(III)

(wherein

X represents —CH— or a nitrogen atom;

Y represents —NR$^4$, an oxygen atom or a sulfur atom;

R$^4$ represents a hydrogen atom or an alkyl group having from 1 to 3 carbon atoms;

Z represents a hydrogen atom or a halogen atom;

R$^1$ represents an alkyl group having from 1 to 6 carbon atoms optionally substituted with an alkoxy group having from 1 to 6 carbon atoms or a cycloalkyl group having from 3 to 7 carbon atoms; a cycloalkyl group having from 3 to 7 carbon atoms optionally substituted by an alkyl group having from 1 to 3 carbon atoms; a phenyl group optionally substituted with one or more substituents alpha; or a group Het1 optionally substituted with one or more substituents alpha;

Het1 represents a heterocyclic group having from 4 to 7 ring atoms which contains either from 1 to 4 nitrogen ring heteroatoms, or from 0 to 2 nitrogen ring heteroatoms and 1 oxygen or sulfur ring heteroatom;

R$^2$ and R$^3$ independently represent a hydrogen atom or an alkyl group having from 1 to 3 carbon atoms; or R$^2$ and R$^3$ groups together form an alkylene chain having from 3 to 6 carbon atoms; and said substituent alpha is selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxyalkyl groups having from 1 to 4 carbon atoms, alkoxyalkyl groups having from 1 to 4 carbon atoms in each of the alkoxy and alkyl groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsulfonylamino groups having from 1 to 4 carbon atoms, cycloalkyl groups having from 3 to 7 carbon atoms and a mono- or di-alkylaminocarbonyl groups having from 1 to 6 carbon atoms; or when formula (III) includes a hydroxy group and/or a carboxy group, the hydroxy group and the carboxy group may be independently esterified to form a pharmaceutically acceptable ester); and

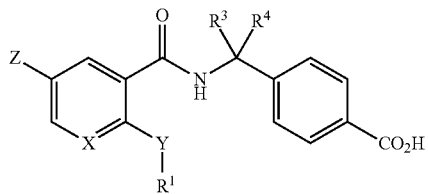

(IV)

(wherein

X represents —CH or a nitrogen atom;

Y represents NR$^4$, an oxygen atom or a sulfur atom;

R$^4$ represents a hydrogen atom or an alkyl group having from 1 to 3 carbon atoms;

Z represents a hydrogen atom or a halogen atom;

R$^1$ represents an alkyl group having from 1 to 6 carbon atoms optionally substituted with 1 to 2 groups independently selected from an alkoxy group having from 1 to 6 carbon atoms, a trifluoromethyl group, an alkanoyl group having from 2 to 5 carbon atoms, a cycloalkyl group having from 3 to 7 carbon atoms, a phenyl group, a phenoxy group, a heterocyclic group and a heteroaryl group; a cycloalkyl group having from 3 to 7 carbon atoms optionally substituted with an alkyl group having from 1 to 3 carbon atoms; or a heterocyclic group;

R$^2$ and R$^3$ independently represent a hydrogen atom or an alkyl group having from 1 to 3 carbon atoms; or R$^2$ and R$^3$ groups together form an alkylene chain having from 3 to 6 carbon atoms;

said heteroaryl group is a 4 to 7-membered aromatic ring system having either from 1 to 4 nitrogen ring heteroatoms, or 0 to 2 nitrogen ring heteroatoms and 1 oxygen or sulfur ring heteroatom;

said heterocyclic group is a 4 to 7-membered saturated ring system having either from 1 to 4 nitrogen ring heteroatoms, or 0 to 2 nitrogen ring heteroatoms and 1 oxygen or sulfur ring heteroatom;

said phenyl group, phenoxy group and heteroaryl group referred to in the definition of R$^1$ are unsubstituted or are substituted by at least one substituent selected from the group consisting of substituents alpha; and said substituent alpha is selected from the group consisting of halogen atoms, alkyl groups having from 1 to 4 carbon atoms, haloalkyl groups having from 1 to 4 carbon atoms, hydroxyl groups, alkoxy groups having from 1 to 4 carbon atoms, haloalkoxy groups having from 1 to 4 carbon atoms, cyano groups, hydroxyalkyl groups having from 1 to 4 carbon atoms, alkoxyalkyl groups having from 1 to 4 carbon atoms in each of the alkoxy and alkyl groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsulfonylamino groups having from 1 to 4 carbon atoms, cycloalkyl groups having from 3 to 7 carbon atoms and a mono- or di-alkylaminocarbonyl groups having from 1 to 6 carbon atoms; or when formula (IV) includes OH and/or CO$_2$H, said OH and CO$_2$H may be independently esterified to form a pharmaceutically acceptable ester).

Preferably, compounds of the present invention, which are useful for the treatment of cancer, in formula (I) are:

3-[2-(4-{2-ethyl-5,7-dimethyl-3H-imidazo[4,5-b]pyridin-3-yl}phenyl)ethyl]-1-[(4-methylbenzene)sulfonyl]urea;

1-(4-{2-ethyl-4,6-dimethyl-1H-imidazo[4,5-c]pyridin-1-yl}phenyl)propan-2-yl N-[(4-methylbenzene)sulfonyl]carbamate;

3-[2-(4-{2-ethyl-4,6-dimethyl-1H-imidazo[4,5-c]pyridin-1-yl}phenyl)ethyl]-1-[(4-methylbenzene)sulfonyl]urea;

1-{2-[4-(5-acetyl-2-ethyl-1H-1,3-benzothiazol-1-yl)phenyl]ethyl}-3-[(4-methylbenzene)sulfonyl]urea;

3-{2-[4-(2-ethyl-5-methoxy-1H-1,3-benzothiazol-1-yl)phenyl]ethyl}-1-[(4-methylbenzene)sulfonyl]urea;

2-{4-[6-chloro-2-ethyl-5-(trifluoromethyl)-1H-1,3-benzothiazol-1-yl]phenyl}ethyl N-[(4-methylbenzene)sulfonyl]carbamate;

3-{2-[4-(6-chloro-5-cyano-2-ethyl-1H-1,3-benzothiazol-1-yl)phenyl]ethyl}-1-[(4-methylbenzene)sulfonyl]urea;

2-(4-{2-ethyl-4,6-dimethyl-1H-imidazo[4,5-c]pyridin-1-yl}phenyl)ethyl N-[(4-methylbenzene)sulfonyl]carbamate;

2-(4-{2-butyl-4,6-dimethyl-1H-imidazo[4,5-c]pyridin-1-yl}phenyl)ethyl N-[(4-methylbenzene)sulfonyl]carbamate;

2-(4-{2-tertiary-butyl-4,6-dimethyl-1H-imidazo[4,5-c]pyridin-1-yl}phenyl)ethyl N-[(4-methylbenzene)sulfonyl]carbamate;

2-(4-{2-amino-5,7-dimethyl-3H-imidazo[4,5-b]pyridin-3-yl}phenyl)ethyl N-[(4-methylbenzene)sulfonyl]carbamate;

3-{2-[4-(6-chloro-2-ethyl-5-methanesulfonyl-1H-1,3-benzothiazol-1-yl)phenyl]ethyl}-1-[(4-methylbenzene)sulfonyl]urea;

2-[4-(5-carbamoyl-6-chloro-2-ethyl-1H-1,3-benzothiazol-1-yl)phenyl]ethyl N-[(4-methylbenzene)sulfonyl]carbamate;

1-(2-{4-[2-ethyl-5-(1-hydroxyethyl)-1H-1,3-benzothiazol-1-yl]phenyl}ethyl)-3-[(4-methylbenzene)sulfonyl]urea;

1-(2-{4-[2-ethyl-5-(2-hydroxypropan-2-yl)-1H-1,3-benzothiazol-1-yl]phenyl}ethyl)-3-[(4-methylbenzene)sulfonyl]urea;

1-(2-{4-[6-chloro-2-(2-hydroxypropan-2-yl)-5-(trifluoromethyl)-1H-1,3-benzothiazol-1-yl]phenyl}ethyl)-3-[(4-methylbenzene)sulfonyl]urea;

N-[1-(6-chloro-1-{4-[2-({[(4-methylbenzene)sulfonyl]carbamoyl}amino)ethyl]phenyl}-5-(trifluoromethyl)-1H-1,3-benzothiazol-2-yl)ethyl]acetamide;

6-chloro-2-ethyl-1-(4-{2-[methyl({[(4-methylbenzene)sulfonyl]carbamoyl})amino]ethyl}phenyl)-1H-1,3-benzothiazol-5-carboxamide;

2-{4-[6-chloro-2-(pyridin-2-yl)-5-(trifluoromethyl)-1H-1,3-benzothiazol-1-yl]phenyl}ethyl N-[(4-methylbenzene)sulfonyl]carbamate;

3-(2-{5-[6-chloro-2-ethyl-5-(trifluoromethyl)-1H-1,3-benzothiazol-1-yl]pyridin-2-yl}ethyl)-1-[(4-methylbenzene)sulfonyl]urea;

2-{4-[6-chloro-2-ethyl-5-(trifluoromethyl)-1H-1,3-benzothiazol-1-yl]phenyl}ethyl N-[(2-chlorobenzene)sulfonyl]carbamate; or 3-(2-{4-[5,7-dimethyl-2-(methylamino)-3H-imidazo[4,5-b]pyridin-3-yl]phenyl}ethyl)-1-[(4-methylbenzene)sulfonyl]urea;

in formula (II) are:

4-((1S)-1-{[5-chloro-2-(4-fluorophenoxy)benzoyl]amino}ethyl)benzoic acid;

4-[(1S)-1-({[5-chloro-2-(4-fluorophenoxy)pyridin-3-yl]carbonyl}amino)ethyl]benzoic acid;

4-[(1S)-1-({[5-chloro-2-(3-cyanophenoxy)pyridin-3-yl]carbonyl}amino)ethyl]benzoic acid;

4-[(1S)-1-({[5-chloro-2-(3-fluorophenoxy)pyridin-3-yl]carbonyl}amino)ethyl]benzoic acid;

4-[(1S)-1-({[5-chloro-2-(3-chlorophenoxy)pyridin-3-yl]carbonyl}amino)ethyl]benzoic acid;

4-((1S)-1-{[5-chloro-2-(3-fluorophenoxy)benzoyl]amino}ethyl)benzoic acid;

4-((1S)-1-{[5-chloro-2-(3-chlorophenoxy)benzoyl]amino}ethyl)benzoic acid;

4-[(1S)-1-({[5-chloro-2-(2-chloro-4-fluorophenoxy)pyridin-3-yl]carbonyl}amino)ethyl]benzoic acid;

4-[(1S)-1-({[5-chloro-2-(2,6-difluorophenoxy)pyridin-3-yl]carbonyl}amino)ethyl]benzoic acid;

4-[(1S)-1-({[5-chloro-2-(3,4-difluorophenoxy)pyridin-3-yl]carbonyl}amino)ethyl]benzoic acid;

4-[(1S)-1-({[5-chloro-2-(2,3-difluorophenoxy)pyridin-3-yl]carbonyl}amino)ethyl]benzoic acid;

4-[(1S)-1-({[5-chloro-2-(2,5-difluorophenoxy)pyridin-3-yl]carbonyl}amino)ethyl]benzoic acid;

4-[(1S)-1-({[5-chloro-2-(2-chloro-5-fluorophenoxy)pyridin-3-yl]carbonyl}amino)ethyl]benzoic acid;

4-[(1S)-1-({[5-chloro-2-(3-methylphenoxy)pyridin-3-yl]carbonyl}amino)ethyl]benzoic acid;

4-[(1S)-1-({[5-chloro-2-(3,5-difluorophenoxy)pyridin-3-yl]carbonyl}amino)ethyl]benzoic acid;

4-((1S)-1-{[5-chloro-2-(2,3-difluorophenoxy)benzoyl]amino}ethyl)benzoic acid;

4-((1S)-1-{[5-chloro-2-(3,4-difluorophenoxy)benzoyl]amino}ethyl)benzoic acid;

4-[(1S)-1-({[5-chloro-2-(3-chloro-5-fluorophenoxy)pyridin-3-yl]carbonyl}amino)ethyl]benzoic acid;

4-((1S)-1-{[5-chloro-2-(3,5-difluorophenoxy)benzoyl]amino}ethyl)benzoic acid;

4-((1S)-1-{[5-chloro-2-(2,5-difluorophenoxy)benzoyl]amino}ethyl)benzoic acid;

4-[(1S)-1-({[5-chloro-2-(3-chloro-5-methylphenoxy)pyridin-3-yl]carbonyl}amino)ethyl]benzoic acid;

4-((1S)-1-{[5-chloro-2-(3-methylphenoxy)benzoyl]amino}ethyl)benzoic acid;

((1S)-1-{[5-chloro-2-(3-chloro-5-fluorophenoxy)benzoyl]amino}ethyl)benzoic acid;

4-((1S)-1-{[5-chloro-2-(2,6-difluorophenoxy)benzoyl]amino}ethyl)benzoic acid;

4-((1S)-1-{[(5-chloro-2-phenoxypyridin-3-yl)carbonyl]amino}ethyl)benzoic acid;

4-[(1S)-1-({[5-chloro-2-(2,3-dichlorophenoxy)pyridin-3-yl]carbonyl}amino)ethyl]benzoic acid;

4-[(1S)-1-({[5-chloro-2-(3,4-dichlorophenoxy)pyridin-3-yl]carbonyl}amino)ethyl]benzoic acid;

4-[(1S)-1-({[5-chloro-2-(3,5-dichlorophenoxy)pyridin-3-yl]carbonyl}amino)ethyl]benzoic acid; or 4-[(1S)-1-({[5-chloro-2-(3-fluoro-4-methylphenoxy)pyridin-3-yl]carbonyl}amino)ethyl]benzoic acid;

in formula (III) are:

4-[(1S)-1-({5-chloro-2-[(4-chlorophenoxy)methyl]benzoyl}amino)ethyl]benzoic acid;

4-[(1S)-1-({5-chloro-2-[(4-methylphenoxy)methyl]benzoyl}amino)ethyl]benzoic acid;

4-[(1S)-1-({5-chloro-2-[(3-chlorophenoxy)methyl]benzoyl}amino)ethyl]benzoic acid;

4-[(1S)-1-({5-chloro-2-[(4-fluorophenoxy)methyl]benzoyl}amino)ethyl]benzoic acid;

4-[(1S)-1-({5-chloro-2-[(2,3-difluorophenoxy)methyl]benzoyl}amino)ethyl]benzoic acid;

4-[(1S)-1-({5-chloro-2-[(3,4-difluorophenoxy)methyl]benzoyl}amino)ethyl]benzoic acid;

4-[(1S)-1-({5-chloro-2-[(2,4-difluorophenoxy)methyl]benzoyl}amino)ethyl]benzoic acid;

4-{(1S)-1-[({5-chloro-2-[(3-chlorophenoxy)methyl]pyridin-3-yl}carbonyl)amino]ethyl}benzoic acid;
4-[(1S)-1-({5-chloro-2-[(2-chlorophenoxy)methyl]benzoyl}amino)ethyl]benzoic acid;
4-[(1S)-1-({5-chloro-2-[(3,5-difluorophenoxy)methyl]benzoyl}amino)ethyl]benzoic acid;
4-{(1S)-1-[({5-chloro-2-[(4-chlorophenoxy)methyl]pyridin-3-yl}carbonyl)amino]ethyl}benzoic acid;
4-[(1S)-1-({5-chloro-2-[(3-fluorophenoxy)methyl]benzoyl}amino)ethyl]benzoic acid;
4-[(1S)-1-({5-chloro-2-[(2,6-difluorophenoxy)methyl]benzoyl}amino)ethyl]benzoic acid;
4-[(1S)-1-({5-chloro-2-[(2-fluorophenoxy)methyl]benzoyl}amino)ethyl]benzoic acid;
4-[(1S)-1-({5-chloro-2-[(2,5-difluorophenoxy)methyl]benzoyl}amino)ethyl]benzoic acid;
4-{(1S)-1-[({2-[(4-chlorophenoxy)methyl]-5-fluoropyridin-3-yl}carbonyl)amino]ethyl}benzoic acid; or
4-{(1S)-1-({5-chloro-2-[(cyclohexylmethoxy)methyl]benzoyl}amino)ethyl}benzoic acid; and
in formula (IV) are:
4-[(1S)-1-({5-chloro-2-[(2-chlorobenzyl)oxy]benzoyl}amino)ethyl]benzoic acid;
4-[(1S)-1-({5-chloro-2-[2-(2-methylphenyl)ethoxy]benzoyl}amino)ethyl]benzoic acid;
4-[(1S)-1-({5-chloro-2-[2-(4-methylphenyl)ethoxy]benzoyl}amino)ethyl]benzoic acid;
4-[(1S)-1-({5-chloro-2-[(3-chlorobenzyl)oxy]benzoyl}amino)ethyl]benzoic acid;
4-[(1S)-1-({5-chloro-2-[(4-chlorobenzyl)oxy]benzoyl}amino)ethyl]benzoic acid;
4-((1S)-1-{[5-chloro-2-(cyclobutylmethoxy)benzoyl]amino}ethyl)benzoic acid;
4-((1S)-1-{[5-chloro-2-(cyclohexyloxy)benzoyl]amino}ethyl)benzoic acid;
4-[(1S)-1-({5-chloro-2-[(2-cyanobenzyl)oxy]benzoyl}amino)ethyl]benzoic acid;
4-[(1S)-1-({5-chloro-2-[2-(4-fluorophenyl)ethoxy]benzoyl}amino)ethyl]benzoic acid;
4-((1S)-1-{[5-chloro-2-(3-methylbutoxy)benzoyl]amino}ethyl)benzoic acid;
4-[(1S)-1-({5-chloro-2-[(4-fluorobenzyl)oxy]benzoyl}amino)ethyl]benzoic acid;
4-[(1S)-1-({5-chloro-2-[2-(2-fluorophenyl)ethoxy]benzoyl}amino)ethyl]benzoic acid;
4-[(1S)-1-({5-chloro-2-[(2,5-difluorobenzyl)oxy]benzoyl}amino)ethyl]benzoic acid;
4-[({5-chloro-2-[2-(2-methylphenyl)ethoxy]benzoyl}amino)methyl]benzoic acid;
4-[(1S)-1-({5-chloro-2-[(2-chloro-4-fluorobenzyl)oxy]benzoyl}amino)ethyl]benzoic acid;
4-((1S)-1-{[5-chloro-2-(2-phenoxyethoxy)benzoyl]amino}ethyl)benzoic acid;
4-[(1S)-1-({5-chloro-2-[(3,4-difluorobenzyl)oxy]benzoyl}amino)ethyl]benzoic acid;
4-[(1S)-1-({5-chloro-2-[(4-chloro-2-fluorobenzyl)oxy]benzoyl}amino)ethyl]benzoic acid;
4-{(1S)-1-[({5-chloro-2-[(4-chlorobenzyl)oxy]pyridin-3-yl}carbonyl)amino]ethyl}benzoic acid;
4-((1S)-1-{[2-(benzyloxy)-5-chlorobenzoyl]amino}ethyl)benzoic acid;
4-{(1S)-1-[({5-chloro-2-[(2-chlorobenzyl)oxy]pyridin-3-yl}carbonyl)amino]ethyl}benzoic acid;
4-{(1S)-1-[({5-chloro-2-[2-(4-chlorophenyl)ethoxy]pyridin-3-yl}carbonyl)amino]ethyl}benzoic acid;
4-[(1S)-1-({5-chloro-2-[(3,5-difluorobenzyl)oxy]benzoyl}amino)ethyl]benzoic acid; or
4-[(1S)-1-({5-chloro-2-[2-(2,6-difluorophenyl)ethoxy]benzoyl}amino)ethyl]benzoic acid; or
a pharmaceutically acceptable salt thereof.

More preferably, compounds of the present invention, which are useful for the treatment of cancer, in formula (I) are:
3-[2-(4-{2-ethyl-5,7-dimethyl-3H-imidazo[4,5-b]pyridin-3-yl}phenyl)ethyl]-1-[(4-methylbenzene)sulfonyl]urea;
3-[2-(4-{2-ethyl-4,6-dimethyl-1H-imidazo[4,5-c]pyridin-1-yl}phenyl)ethyl]-1-[(4-methylbenzene)sulfonyl]urea;
1-{2-[4-(5-acetyl-2-ethyl-1H-1,3-benzothiazol-1-yl)phenyl]ethyl}-3-[(4-methylbenzene)sulfonyl]urea;
3-{2-[4-(2-ethyl-5-methoxy-1H-1,3-benzothiazol-1-yl)phenyl]ethyl}-1-[(4-methylbenzene)sulfonyl]urea;
2-{4-[6-chloro-2-ethyl-5-(trifluoromethyl)-1H-1,3-benzothiazol-1-yl]phenyl}ethyl N-[(4-methylbenzene)sulfonyl]carbamate;
3-{2-[4-(6-chloro-5-cyano-2-ethyl-1H-1,3-benzothiazol-1-yl)phenyl]ethyl}-1-[(4-methylbenzene)sulfonyl]urea;
2-(4-{2-ethyl-4,6-dimethyl-1H-imidazo[4,5-c]pyridin-1-yl}phenyl)ethyl N-[(4-methylbenzene)sulfonyl]carbamate;
2-(4-{2-tert-butyl-4,6-dimethyl-1H-imidazo[4,5-c]pyridin-1-yl}phenyl)ethyl N-[(4-methylbenzene)sulfonyl]carbamate;
2-[4-(5-carbamoyl-6-chloro-2-ethyl-1H-1,3-benzothiazol-1-yl)phenyl]ethyl N-[(4-methylbenzene)sulfonyl]carbamate;
1-(2-{4-[2-ethyl-5-(1-hydroxyethyl)-1H-1,3-benzothiazol-1-yl]phenyl}ethyl)-3-[(4-methylbenzene)sulfonyl]urea;
1-(2-{4-[6-chloro-2-(2-hydroxypropan-2-yl)-5-(trifluoromethyl)-1H-1,3-benzothiazol-1-yl]phenyl}ethyl)-3-[(4-methylbenzene)sulfonyl]urea;
2-{4-[6-chloro-2-(pyridin-2-yl)-5-(trifluoromethyl)-1H-1,3-benzothiazol-1-yl]phenyl}ethyl N-[(4-methylbenzene)sulfonyl]carbamate;
3-(2-{5-[6-chloro-2-ethyl-5-(trifluoromethyl)-1H-1,3-benzothiazol-1-yl]pyridin-2-yl}ethyl)-1-[(4-methylbenzene)sulfonyl]urea;
2-{4-[6-chloro-2-ethyl-5-(trifluoromethyl)-1H-1,3-benzothiazol-1-yl]phenyl}ethyl N-[(2-chlorobenzene)sulfonyl]carbamate; or
3-(2-{4-[5,7-dimethyl-2-(methylamino)-3H-imidazo[4,5-b]pyridin-3-yl]phenyl}ethyl)-1-[(4-methylbenzene)sulfonyl]urea;
in formula (II) are:
4-((1S)-1-{[5-chloro-2-(4-fluorophenoxy)benzoyl]amino}ethyl)benzoic acid;
4-[(1S)-1-({[5-chloro-2-(4-fluorophenoxy)pyridin-3-yl]carbonyl}amino)ethyl]benzoic acid;
4-[(1S)-1-({[5-chloro-2-(3-cyanophenoxy)pyridin-3-yl]carbonyl}amino)ethyl]benzoic acid;
4-[(1S)-1-({[5-chloro-2-(3-fluorophenoxy)pyridin-3-yl]carbonyl}amino)ethyl]benzoic acid;
4-[(1S)-1-({[5-chloro-2-(3-chlorophenoxy)pyridin-3-yl]carbonyl}amino)ethyl]benzoic acid;
4-((1S)-1-{[5-chloro-2-(3-fluorophenoxy)benzoyl]amino}ethyl)benzoic acid;
4-((1S)-1-{[5-chloro-2-(3-chlorophenoxy)benzoyl]amino}ethyl)benzoic acid;
4-[(1S)-1-({[5-chloro-2-(2-chloro-4-fluorophenoxy)pyridin-3-yl]carbonyl}amino)ethyl]benzoic acid;
4-[(1S)-1-({[5-chloro-2-(3,4-difluorophenoxy)pyridin-3-yl]carbonyl}amino)ethyl]benzoic acid;
4-[(1S)-1-({[5-chloro-2-(2,3-difluorophenoxy)pyridin-3-yl]carbonyl}amino)ethyl]benzoic acid;

4-((1S)-1-{[5-chloro-2-(2,3-difluorophenoxy)benzoyl]
amino}ethyl)benzoic acid;
4-((1S)-1-{[5-chloro-2-(3,4-difluorophenoxy)benzoyl]
amino}ethyl)benzoic acid; or
4-[(1S)-1-({[5-chloro-2-(3-chloro-5-fluorophenoxy)pyridin-3-yl]carbonyl}amino)ethyl]benzoic acid;
in formula (III) are:
4-[(1S)-1-({5-chloro-2-[(4-chlorophenoxy)methyl]
benzoyl}amino)ethyl]benzoic acid;
4-[(1S)-1-({5-chloro-2-[(3-chlorophenoxy)methyl]
benzoyl}amino)ethyl]benzoic acid;
4-[(1S)-1-({5-chloro-2-[(4-fluorophenoxy)methyl]
benzoyl}amino)ethyl]benzoic acid;
4-[(1S)-1-({5-chloro-2-[(3,4-difluorophenoxy)methyl]
benzoyl}amino)ethyl]benzoic acid;
4-[(1S)-1-({5-chloro-2-[(2,4-difluorophenoxy)methyl]
benzoyl}amino)ethyl]benzoic acid;
4-{(1S)-1-[({5-chloro-2-[(3-chlorophenoxy)methyl]pyridin-3-yl}carbonyl)amino]ethyl}benzoic acid;
4-[(1S)-1-({5-chloro-2-[(3,5-difluorophenoxy)methyl]
benzoyl}amino)ethyl]benzoic acid;
4-[(1S)-1-({5-chloro-2-[(3-fluorophenoxy)methyl]
benzoyl}amino)ethyl]benzoic acid;
4-{(1S)-1-[({2-[(4-chlorophenoxy)methyl]-5-fluoropyridin-3-yl}carbonyl)amino]ethyl}benzoic acid; or
4-{(1S)-1-({5-chloro-2-[(cyclohexylmethoxy)methyl]
benzoyl}amino)ethyl}benzoic acid; and
in formula (IV) are:
4-[(1S)-1-({5-chloro-2-[(2-chlorobenzyl)oxy]
benzoyl}amino)ethyl]benzoic acid;
4-[(1S)-1-({5-chloro-2-[(3-chlorobenzyl)oxy]
benzoyl}amino)ethyl]benzoic acid;
4-[(1S)-1-({5-chloro-2-[(4-chlorobenzyl)oxy]
benzoyl}amino)ethyl]benzoic acid;
4-((1S)-1-{[5-chloro-2-(cyclobutylmethoxy)benzoyl]
amino}ethyl)benzoic acid;
4-((1S)-1-{[5-chloro-2-(cyclohexyloxy)benzoyl]
amino}ethyl)benzoic acid;
4-[(1S)-1-({5-chloro-2-[(2-cyanobenzyl)oxy]
benzoyl}amino)ethyl]benzoic acid;
4-[(1S)-1-({5-chloro-2-[2-(4-fluorophenyl)ethoxy]
benzoyl}amino)ethyl]benzoic acid;
4-[(1S)-1-({5-chloro-2-[(4-fluorobenzyl)oxy]
benzoyl}amino)ethyl]benzoic acid;
4-[(1S)-1-({5-chloro-2-[2-(2-fluorophenyl)ethoxy]
benzoyl}amino)ethyl]benzoic acid;
4-[(1S)-1-({5-chloro-2-[(2-chloro-4-fluorobenzyl)oxy]
benzoyl}amino)ethyl]benzoic acid;
4-[(1S)-1-({5-chloro-2-[(4-chloro-2-fluorobenzyl)oxy]
benzoyl}amino)ethyl]benzoic acid;
4-{(1S)-1-[({5-chloro-2-[(4-chlorobenzyl)oxy]pyridin-3-yl}carbonyl)amino]ethyl}benzoic acid;
4-{(1S)-1-[({5-chloro-2-[(2-chlorobenzyl)oxy]pyridin-3-yl}carbonyl)amino]ethyl}benzoic acid;
4-{(1S)-1-[({5-chloro-2-[2-(4-chlorophenyl)ethoxy]pyridin-3-yl}carbonyl)amino]ethyl}benzoic acid;
4-[(1S)-1-({5-chloro-2-[(3,5-difluorobenzyl)oxy]
benzoyl}amino)ethyl]benzoic acid; or
4-[(1S)-1-({5-chloro-2-[2-(2,6-difluorophenyl)ethoxy]
benzoyl}amino)ethyl]benzoic acid; or
a pharmaceutically acceptable salt thereof.

These compounds are disclosed in WO 02/32900, WO 2005/021508, WO 05/105732, and WO 2005/105733.

Pharmaceutically acceptable salts include acid addition salts and base salts thereof. Suitable acid addition salts are usually formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are usually formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I), (II), (III), or (IV) may be readily prepared by mixing together solutions of the compound of formula (I), (II), (III), or (IV) and the desired acid or base, as appropriate. The salt may be precipitated from solution and be collected by filtration, or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Hereinafter, all references to compounds of formula (I), (II), (III), or (IV) include references to salts, solvates and complexes thereof and to solvates and complexes of salts thereof.

The compounds of the invention include compounds of the present invention as hereinbefore defined, polymorphs, prodrugs, and isomers thereof (including optical, geometric and tautomeric isomers) and isotopically-labeled compounds of the present invention as hereinafter defined.

As stated above, the invention includes all polymorphs of the compounds of the present invention as hereinbefore defined.

Also within the scope of the invention are so-called 'prodrugs' of the compounds of formula (I), (II), (III), or (IV). Thus, certain derivatives of compounds of formula (I), (II), (III), or (IV) which may have little or no pharmacological activity themselves can, when administered into or onto the body, be converted into compounds of formula (I), (II), (III), or (IV) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B. Roche, American Pharmaceutical Association).

Prodrugs in accordance with the invention can, for example, be produced by replacing appropriate functionalities present in the compounds of formula (I), (II), (III), or (IV) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of the present invention contains a carboxylic acid functionality (—COOH), an ester thereof obtainable by, for example, replacement of the hydrogen with $(C_1-C_8)$alkyl;

(ii) where the compound of the present invention contains an alcohol functionality (—OH), an ether thereof obtainable by, for example, replacement of the hydrogen with $(C_1-C_6)$alkanoyloxymethyl; and (iii) where the compound of the present invention contains a primary or secondary amino functionality (—$NH_2$ or —NHR where R≠H), an amide thereof obtainable by, for example, replacement of one or both hydrogens with $(C_1-C_{10})$alkanoyl.

Further examples of substituent groups other than the foregoing examples are known to skilled in the art and can be found in the aforementioned references, but not limited to them.

Finally, certain compounds of formula (I), (II), (III), or (IV) may themselves also act as prodrugs of other compounds of the present invention.

Compounds of the present invention containing one or more asymmetric carbon atoms can exist as two or more stereoisomers. Where a compound of the present invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of the present invention, including compounds exhibiting more than/equal to two type of isomerism, and mixtures of one or more thereof. Also included are acid addition salts or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor and resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the present invention contains an acidic or basic moiety, an acid or base such as tartaric acid or 1-phenylethylamine. The resulting diastereomeric mixture may be separated by chromatography and/or fractional crystallization and one or both of the diastereoisomers can be converted to the corresponding pure enantiomer(s) by means well known to a skilled person.

Chiral compounds of the present invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50 (w/w) % isopropanol, typically from 2 to 20 (w/w) %, and from 0 to 5 (w/w) % of an alkylamine, typically 0.1 (w/w) % diethylamine. Concentration of the eluate affords the enriched mixture.

Stereoisomeric conglomerates may be separated by conventional techniques known to those skilled in the art—see, for example, *Stereochemistry of Organic Compounds* by E L Eliel (Wiley, N.Y., 1994).

The present invention includes all pharmaceutically acceptable isotopically-labeled compounds of the present invention wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2H$ and $^3H$, carbon, such $^{11}C$, $^{13}C$ and $^{14}C$, chlorine, such as $^{36}Cl$, fluorine, such as $^{18}F$ iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labeled compounds of the present invention, for example, those incorporating a radioactive isotope, are useful in drug and/or substrate tissue distribution studies associated with cancer therapy which includes diagnosis, alleviation of symptoms, improvement of QOL, and prophylaxis. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the present invention include those wherein the solvent for crystallization may be isotopically substituted, e.g. $D_2O$, $d_6$-acetone, $d_6$-DMSO.

Compounds of the present invention intended for pharmaceutical use may be administered as crystalline or amorphous products. They may be obtained, for example, as solid plugs, powders, or films by methods such as precipitation, crystallization, freeze drying, spray drying, and evaporative drying. Microwave or radio frequency drying may be used for this purpose.

They may be administered alone or in combination with one or more other compounds of the invention or in combination with one or more other drugs (second therapeutic agent (second active agent)) (or as any combination thereof). Generally, they will be administered as a formulation in association with one or more pharmaceutically acceptable additives. The term "additive" is used herein to describe any ingredient other than the compound(s) of the invention. The choice of additive will to a large extent depend on factors such as the particular mode of administration, the effect of the additive on solubility and stability, and the nature of the dosage form.

Thus, the present invention provides a combination of a compound of this invention, a solvate thereof, or a prodrug thereof with one or more other pharmaceutically active agents (or compound group, the second therapeutic agent). In addition, the present invention provides a pharmaceutical composition comprising such a combination in association with a pharmaceutically acceptable additive, diluent, or carrier, particularly for the treatment of cancer which EP4 antagonists relate to. Also, the present invention provides a kit comprising: a first pharmaceutical composition comprising a compound of general formula (I), (II), (III), or (IV), or a pharmaceutically acceptable salt thereof; a second active agent; and a container.

A kit for the treatment of cancer, which comprises the compound of general formula (I), (II), (III), or (IV), or the pharmaceutically acceptable salt thereof, is also one of the inventions. A commercial package comprising a pharmaceutical composition containing the compound of general formula (I), (II), (III), or (IV), or the pharmaceutically acceptable salt thereof and a written matter associated with the pharmaceutical composition, wherein the written matter states that said pharmaceutical composition can or should be used for treating cancer is also one of the inventions.

DEFINITION OF TERM

The skilled in the art can well understand the term in the present specification and claims attached, but the following terms have meanings as described below.

The term "EP4 receptor activity" or "EP4 activity", as used herein, means elevation of cAMP in association with PGE2 stimulation mediated by EP4 receptor.

The term "selective" EP4 receptor antagonist, as used herein, means a EP4 receptor antagonist with such an ability in inhibiting EP4 activity that the $IC_{50}$, which is measured according to the standard method known in the present field, shows at least 10 times, preferably 100 times lower than $IC_{50}$ of EP1, EP2, or EP3 activity.

The terms "halo" and "halogen atom", as used herein, refer to F, Cl, Br or I, preferably F or Cl.

The term "alkyl", as used herein, means a straight or branched saturated monovalent hydrocarbon radical including, but not limited to, methyl, ethyl, propyl, isopropyl, n-butyl, iso-butyl, sec-butyl, tert-butyl, neopentyl and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butyryl, 2-butyryl and the like.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "alkoxy", as used herein, means an O-alkyl group wherein "alkyl" is as defined above, including, but not limited to methoxy, ethoxy, n-propoxy, iso-propoxy, n-butoxy, iso-butoxy, secondary-butoxy, tertiary-butoxy and the like.

In addition, for example, $C_{1-4}$ alkyl, as used herein, has the same meaning as alkyl having one to four carbon atoms.

The term "alkylene", as used herein, means saturated hydrocarbon (straight chain or branched) wherein a hydrogen atom is removed from each of the terminal carbons such as methylene, ethylene, propylene, butylene, pentylene, hexylene and the like.

The term "cycloalkylene", as used herein, means a divalent cycloalkyl group including, but not limited to, cyclopropylene, cyclobutylene, cyclopentylene, cyclohexylene, cycloheptylene and the like.

The term "alkenylene", as used herein, means a straight or branched hydrocarbon chain spacer radical having at least one double bond including, but not limited to, —CH═CH—, —CH═CHCH—, —CH═CHCH($CH_3$)—, and the like.

The term "alkynylene", as used herein, means a straight or branched hydrocarbon chain spacer radical having at least one triple bond including, but not limited to, —C≡C—, —C—C≡C$CH_2$—, —C≡CCH($CH_3$)—, and the like.

The term "alkanoyl", as used herein, means a group having carbonyl such as R'—C(O)— wherein R' is $C_{1-4}$ alkyl or $C_{3-4}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)— and the like.

The term "haloalkyl", as used herein, means an alkyl radical which is substituted by a halogen atom as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

The term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

The term "aryl", as used herein, means an aromatic radical including, but not limited to, phenyl, naphthyl, tetrahydronaphthyl, indanyl, biphenyl and the like.

The term "monocyclic aromatic ring", as used herein, means a monocyclic aromatic carbocyclic or heterocyclic ring (containing 0 to 4 heteroatoms selected from O, N and S) including, but not limited to, phenyl, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl and the like.

The term "bicyclic aromatic ring", as used herein, means a monocyclic or bicyclic aromatic carbocyclic or heterocyclic ring (containing 0 to 4 heteroatoms selected from O, N and S) including, but not limited to, naphthyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl quinoxalinyl and the like.

The term "tricyclic ring", as used herein, means a saturated carbocyclic radical including, but not limited to, adamantyl, tricyclo[$5.2.1.0^{2,6}$]decyl, and the like.

The term "two adjacent L groups are optionally joined together to form an alkylene chain having 3 or 4 members in which one or two (non-adjacent) carbon atoms are optionally replaced by oxygen atom(s)", as used herein, means, but not limited to, —O—$CH_2$—O—, —$CH_2$—O—$CH_2$—, —O—$CH_2CH_2$—, $CH_2CH_2$—O—, —O—$CH_2CH_2$—O—, —CH$_2$CH$_2$CH$_2$—O—, —O—CH$_2$CH$_2$CH$_2$—, —CH$_2$—O—CH$_2$CH$_2$—, —CH$_2$CH$_2$—O—CH$_2$—, and the like. The term "two adjacent L groups" means two L groups which bind to separate carbon atoms adjacent to each other. The said above "two non-adjacent carbon atoms" means that they may be two adjacent carbon atoms or may be two non-adjacent carbon atoms.

The term "ester" means a protecting group which can be cleaved in vivo by a biological method such as hydrolysis and forms a free acid or a salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of groups for an ester of a carboxyl group or a hydroxy group include: (1) aliphatic alkanoyl groups, for example: alkanoyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups such as chloroacetyl, dichloroacetyl, trichloroacetyl, and trifluoroacetyl groups; alkoxyalkanoyl groups such as a methoxyacetyl group; and unsaturated alkanoyl groups such as acryloyl, propioloyl, methacryloyl, crotonoyl, isocrotonoyl and (E)-2-methyl-2-butenoyl groups;

(2) aromatic alkanoyl groups, for example: arylcarbonyl groups such as benzoyl, alpha-naphthoyl and beta-naphthoyl groups; halogenated arylcarbonyl groups such as 2-bromobenzoyl and 4-chlorobenzoyol groups; alkylated arylcarbonyl groups such as 2,4,6-trimethylbenzoyl and 4-toluoyl groups; alkoxylated arylcarbonyl groups such as a 4-anisoyl group; nitrated arylcarbonyl groups such as 4-nitrobenzoyl and 2-nitrobenzoyl groups; alkoxycarbonylated arylcarbonyl groups such as a 2-(methoxycarbonyl)benzoyl group; and arylated arylcarbonyl groups such as a 4-phenylbenzoyl group;

(3) alkoxycarbonyl groups, for example: alkoxycarbonyl groups such as methoxycarbonyl, ethoxycarbonyl, propoxycarbonyl, butoxycarbonyl, sec-butoxycarbonyl, t-butoxycarbonyl and isobutoxycarbonyl groups; and halogen- or tri(alkyl)silyl-substituted alkoxycarbonyl groups such as 2,2,2-trichloroethoxycarbonyl and 2-trimethylsilylethoxycarbonyl groups;

(4) tetrahydropyranyl or tetrahydrothiopyranyl groups such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups such as tetrahydrofuran-2-yl and tetrahydrothiofuran-2-yl groups;

(5) silyl groups, for example: tri(alkyl)silyl groups such as trimethylsilyl, triethylsilyl, isopropyldimethylsilyl, t-butyldimethylsilyl, methyldiisopropylsilyl, methyldi-t-butylsilyl and triisopropylsilyl groups; and silyl groups substituted by one or more aryl and alkyl groups such as diphenylmethylsilyl, diphenylbutylsilyl, diphenylisopropylsilyl and phenyldiisopropylsilyl groups;

(6) alkoxymethyl groups, for example: alkoxymethyl groups such as methoxymethyl, 1,1-dimethyl-1-methoxymethyl, ethoxymethyl, propoxymethyl, isopropoxymethyl, butoxymethyl and t-butoxymethyl groups; alkoxylated alkoxymethyl groups such as a 2-methoxyethoxymethyl group; and halo(alkoxy)methyl groups such as 2,2,2-trichloroethoxymethyl and bis(2-chloroethoxy)methyl groups;

(7) substituted ethyl groups, for example: alkoxylated ethyl groups such as 1-ethoxyethyl and 1-(isopropoxy)ethyl groups; and halogenated ethyl groups such as a 2,2,2-trichloroethyl group; and (8) aralkyl groups, for example: alkyl groups substituted by from 1 to 3 aryl groups such as benzyl, alpha-naphthylmethyl, beta-naphthylmethyl, diphenylmethyl, triphenylmethyl, alpha-naphthyldiphenylmethyl and 9-anthrylmethyl groups; alkyl groups substituted by from 1 to 3 substituted aryl groups, where one or more of the aryl groups are substituted by one or more alkyl, alkoxy, nitro, halogen or cyano substituents such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups such as vinyloxycarbonyl; aryloxycarbonyl groups such as phenoxycarbonyl; and aralkyloxycarbonyl groups in which the aryl ring may be substituted by 1 or 2 alkoxy or nitro groups, such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991).

The term 'hydrate' is employed when said solvent is water.

The term "treating" or "treatment", as used herein, refers to reversing, alleviating, inhibiting the progress of, or preventing the disorder or condition to which such term applies, or one or more symptoms of such disorder or condition. The term "treating" or "treatment", as used herein, includes not only shrinkage of grown tumor tissue but also alleviation of symptoms, improvement of QOL, and prophylaxis (radiotherapy, postoperative prevention of recurrence, adjuvant chemotherapy and the like).

Other features and advantages of the invention may be apparent from the following detailed description and the claims. Although particular embodiments of the present invention have been described, various other known or usual changes and modifications in this field fall into the present invention and are within the claims. The present invention also includes the equivalents, changes, uses, or variations, which are from the spirit of the present invention.

A compound of the present invention is administered in an enough amount for reducing cancer metastasis, shrinking cancer, and/or enhancing effectiveness of cancer therapy. Such a therapeutic effective amount varies in accordance with the specific condition to be treated, the patient's condition, the route of administration, the formulation, the field decision, and other factors. In the light of the disclosure, depending on the things known to those skilled in the art, the amount is decided by routine optimization techniques.

A pharmaceutical composition can comprise a compound of general formula (I), (II), (III), or (IV), or a pharmaceutically acceptable salt thereof. Such medicaments are mixed with a pharmaceutically acceptable transport medium or carrier.

As used herein, the language "pharmaceutically acceptable transport medium" includes solvents, dispersion media, coatings, antibacterial and antifungal agents, isotonic and absorption delaying agents, and the like, compatible with pharmaceutical administration. The above medium may also contain other active or inactive ingredients and is targeted to cancer tissues based on the composition.

Therapeutic efficacy of compounds of the present invention can be determined in light of this disclosure by standard therapeutic procedures in cell cultures or experimental animals, e.g., for determining the $ED_{50}$ (the dose therapeutically effective in 50% of the population).

The data obtained from cell culture assays and animal studies can be used in formulating a range of dosage for use in humans. The dosage may vary depending upon the formulation and the route of administration. For any EP4 receptor antagonist used in the method of the invention, the therapeutically effective dose can be estimated initially from cell culture assays. A dose may be formulated in animal models to achieve a desired circulating plasma concentration range based on the $IC_{50}$ as determined in cell culture. Such information can be used to more accurately determine useful doses in humans. Levels in plasma may be measured, for example, by high performance liquid chromatography or mass spectrometer.

It is well known to those skilled in the art that certain factors may influence the dosage and timing required to effectively treat a mammal, the factors including, but not limited to, the severity of the disease or disorder, previous treatments, the general health and/or age of the mammal, and other diseases present. Further, treatment of a mammal with a therapeutically effective amount of the compound of the present invention may include, but not limited to, a single treatment, alternate-day treatment, and a series of treatments.

The precise amount of the compounds administered to a human patient, will be particularly within the responsibility of the attendant physician. However, the dose employed will depend upon a number of factors including the age and sex of the patient, the precise condition being treated and its severity, and the route of administration.

The compounds are conveniently administered in the form of pharmaceutical compositions. Such compositions may conveniently be presented for use in conventional manner in admixture with one or more pharmaceutically acceptable carriers or excipients. Preferably, the pharmaceutical compositions are used for treatment of cancer. The pharmaceutical compositions for the treatment of cancer comprising the compounds of the present invention are also one of the present inventions.

While it is possible for the compounds to be administered as a raw chemical, it is preferable to present it as a pharmaceutical formulation. The formulations comprise the compounds together with one or more acceptable carriers or diluents therefor and optionally other therapeutic ingredients. The carrier(s) must be "acceptable" in the sense of being compatible with the other ingredients of the formulation and not deleterious to the recipient thereof.

A pharmaceutical composition is formulated to meet the desirable route of administration. The administration route is, for example, parenteral (e.g. intravenous, intracutaneous, subcutaneous), oral (e.g. ingestion or inhalation), percutaneous (local), mucosal, rectal, and local (including percutaneous, buccal, and sublingual) administration. The solution or suspension can be prepared by the method described in Remington's Pharmacentical Sciences, ($18^{th}$ ed., Gennaro, ed., Mack Publishing Co., Easton, Pa., (1990)).

The most suitable route may be different depending upon, for example the condition and disorder of the recipient. The formulations may conveniently be presented in unit dosage form and may be prepared by any of the methods well known in the art of pharmacy. All the methods include the step of bringing into association the compound ("active ingredient") with the carrier which constitutes one or more accessory ingredients. In general, the formulations are prepared by uniformly and homogeneously bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active agent or dispersing agent. Moulded tablets may be made by moulding in a suitable machine a mixture of the powdered compound moistened with an inert liquid diluent. The tablets may optionally be coated or scored so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavored base such as sucrose and acacia or tragacanth, and pastilles comprising the active ingredient in a base such as gelatin and glycerin or sucrose and acacia.

The compounds of the present invention or a pharmaceutically acceptable salt thereof may also be formulated as depot preparations. Such long acting formulations may be administered by implantation (for example subcutaneously or intramuscularly) or by intramuscular injection. Thus, for example, the compounds of the present invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may contain other agents conventional in the art in the light of the type of formulation in question, for example those suitable for oral administration such as flavoring agents.

It is also beneficial to use the compound of the present invention or the pharmaceutically acceptable salt thereof in combination with at least one member selected from the steroidal or non-steroidal antiandrogen agent or antiestrogen agent, chemotherapeutic agent, GnRH antagonistic peptide, alpha-reductase inhibitor, alpha-receptor inhibitor, aromatase inhibitor, 17beta-hydroxysteroid dehydrogenase inhibitor, adrenal androgen production inhibitor, kinase inhibitor, drug for hormone therapy, and drug inhibiting cell growth factor or its receptor, among others.

The "chemotherapeutic agent" mentioned above includes ifosfamide, adriamycin, peplomycin, cisplatin, cyclophosphamide, 5-FU, UFT, methotrexate, mitomycin C, mitoxantrone, etc.

The "GnRH antagonistic peptide" mentioned above includes non-oral GnRH antagonistic peptides such as cetrorelix, ganirelix, abarelix, etc.

The "adrenal androgen production inhibitor" mentioned above includes lyase (C17, 20-lyase) inhibitors, etc.

The "kinase inhibitor" mentioned above includes tyrosine kinase inhibitor, etc.

The "drug for hormone therapy" includes antiestrogens, progesterones (e.g., MPA, etc.), androgens, estrogens and antiandrogens, among others.

The "cell growth factor" may be any substance that promotes proliferation of cells and generally includes peptides with molecular weights not over 20,000 which express the action at low concentrations through binding to receptors. Specifically, there can be mentioned (1) EGF (epidermal growth factor) or substances having substantially the same activity (e.g., EGF, heregulin (HER2 ligand), etc.), (2) insulin or substances having substantially the same activity (e.g., insulin, IGF (insulin-like growth factor)-1, IGF-2, etc.), (3) FGF (fibroblast growth factor) or substances having substantially the same activity (aFGF, bFGF, KGF (keratinocyte growth factor), HGF (hepatocyte growth factor), FGF-10, etc.), and (4) other growth factors (e.g., CSF (colony stimulating factor), EPO (erythropoietin), IL-2 (interleukin-2), NGF (nerve growth factor), PDGF (platelet-derived growth factor) and TGF beta (transforming growth factor beta), etc.), among others.

The "cell growth factor receptor" may be any receptor capable of binding to said cell growth factor, including EGF receptor, heregulin receptor (HER2), insulin receptor-1, insulin receptor-2, IGF receptor, FGF receptor-1, FGF receptor-2, etc.

The drug inhibiting cell growth factor mentioned above includes herceptin (anti-HER2 receptor antibody), among others.

The drug inhibiting cell growth factor or its receptor mentioned above includes herbimycin, PD 153035 [e.g., Science, 265 (5175) p 1093, (1994)], etc.

A further class of drugs inhibiting cell growth factor or its receptor includes HER2 inhibitors. The HER2 inhibitor may be any substance that inhibits the activity of HER2 (e.g., kinase activity), thus including an antibody, a low-molecular weight compound (synthetic or natural product), an antisense, an HER2 ligand, heregulin, and any of them as partially modified or mutated in structure. Moreover, it may be a substance which inhibits HER2 activity by inhibiting HER2 receptor (e.g. anti-HER2 receptor antibody).

For prostatic cancer, there is used the compound of the present invention in combination with the GnRH super-agonist, antiandrogen, antiestrogen, chemotherapeutic agent (e.g., ifosfamide, UFT, adriamycin, peplomycin, cisplatin, etc.), GnRH antagonistic peptide, aromatase inhibitor, 17beta-hydroxysteroid dehydrogenase inhibitor, adrenal androgen production inhibitor, kinase inhibitor, drug for hormone therapy such as estrogens (e.g., DSB, EMP, etc.), antiandrogens (e.g., CMA. etc.), etc., drug inhibiting cell growth factor or its receptor, or the like.

For breast cancer, there is used the compound of the present invention in combination with the GnRH super-agonist, antiestrogen, chemotherapeutic agent (e.g., cyclophosphamide, 5-FU, UFT, methotrexate, adriamycin, mitomycin C, mitoxantrone, etc.), GnRH antagonistic peptide, aromatase inhibitor, adrenal androgen production inhibitor, kinase inhibitor, drug for hormone therapy such as antiestrogens (e.g., tamoxifen, etc.), progesterones (e.g., MPA, etc.), androgens, estrogens, etc., drug inhibiting cell growth factor or its receptor, or the like.

For gastroenterological cancer, there is used the compound of the present invention in combination with chemotherapeutic agent (e.g., cyclophosphamide, 5-FU, UFT, methotrexate, levofolinate, gemsitabine, adriamycin, mitomycin C, mitoxantrone, etc.), microtubule inhibitor (e.g., vincristine, paclitaxel, etc.), platinum-containing drug e.g., cisplatin, etc., topoisomerase inhibitor (e.g., irinotecan, etoposide, etc.), COX-2 inhibitor, kinase inhibitor, drug inhibiting cell growth factor or its receptor, or the like.

For pulmonary cancer, there is used the compound of the present invention in combination with chemotherapeutic agent (e.g., cyclophosphamide, 5-FU, UFT, methotrexate, adriamycin, mitomycin C, mitoxantrone, etc.), microtubule inhibitor (e.g., vincristine, paclitaxel, etc.), platinum-containing drug e.g., cisplatin, etc., topoisomerase inhibitor (e.g., irinotecan, etoposide, etc.), kinase inhibitor, drug inhibiting cell growth factor or its receptor, or the like.

Second active agents that are small molecules can also be used to alleviate adverse effects associated with the administration of the compounds of the present invention. However, like some large molecules, many are believed to be capable of providing a synergistic effect when administered with (e.g., before, after or simultaneously) the compounds of the present invention. Examples of small molecule second active agents include, but are not limited to, anti-cancer agents, antibiotics, immunosuppressive agents, and steroids.

Examples of anti-cancer agents include, but are not limited to, alkylating agents, anti-neoplastic agents, anti-metabolites (e.g., folate analogs, purine analogs, adenosine analogs, pyrimidine analogs, and substituted ureas), platinum coordination complexes, topoisomerase II inhibitors, and radiation.

Specific anticancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; capecitabine; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; erlotinib; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gefitinib; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pemetrexed; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanidine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasens®); O$^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide;

roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, rituximab, oblimersen (Genasens®), remicade, docetaxel, celecoxib, melphalan, dexamethasone (Decadron®), steroids, gemcitabine, cisplatin, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEGINTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil), paclitaxel, ganciclovir, adriamycin, estramustine sodium phosphate (Emcyt®), sulindac, and etoposide.

In certain embodiments, the second active agent is etoposide, daunomycin, actinomycin D, mitomycin C, cisplatin, carboplatin, pemetrexed, methotrexate, Ara-C, 5-FU, wortmannin, gemcitabin, geldanamycin or a combination of one or more kinds thereof.

In other embodiments, the second active agent is a supportive care agent. An example of supportive care agent is an antiemetic. Specific antiemetic agents include, but are not limited to, phenothiazines, butyrophenones, benzodiazapines, corticosteroids, serotonin antagonists, cannabinoids, and $NK_1$ receptor antagonists. Examples of phenothiazine antiemetics include, but are not limited to, prochlorperazine and trimethobenzamide. Examples of butyophenone antiemetic include, but are not limited to, haloperidol. Examples of benzodiazapine antiemetic include, but are not limited to, lorazepam. Examples of corticosteroid antiemetic include, but are not limited to, dexamethasone. Examples of serotonin antagonist antiemetic include, but are not limited to, ondansetron, granisetron, and dolasetron. Examples of cannabinoid antiemetic include, but are not limited to, dronabinol. Examples of $NK_1$ receptor antagonists include, but are not limited to, aprepitant. Doses and dosing regimens of antiemetic agents should depend on the specific indication being treated, age and condition of a patient, and severity of adverse effects, and may be adjusted accordingly by those of skill in the art. Examples of doses and dosing regimens can be found, for example, in The Physician's Desk Reference.

The invention also includes combining separate pharmaceutical compositions in a kit form. The kit comprises two or more separate pharmaceutical compositions: a compound of the present invention; and a second active agent as described herein. The kit usually comprises a container for containing the separate compositions such as a divided bottle or a divided foil packet, however, the separate compositions may also be contained within a single, undivided container. The kit form is particularly advantageous when the separate components are preferably administered in different dosage forms (e.g., oral and parenteral), or are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

Exemplary Methods of Combination Therapy

In certain embodiments, the methods provided herein comprise administering the compounds of the present invention in combination with one or more second active agents, and/or in combination with radiation therapy or surgery. The administration of the compounds of the present invention and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., Physicians' Desk Reference.

In one embodiment, the second active agent is administered intravenously or subcutaneously once or twice daily in an amount of from about 1 to about 1,000 mg, from about 5 to about 500 mg, from about 10 to about 375 mg or from about 50 to about 200 mg. In one embodiment, the second active agent is rituximab, oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine or a combination thereof. In certain embodiments, the second active agent is etoposide, daunomycin, actinomycin D, mitomycin C, cisplatin, carboplatin, pemetrexed, methotrexate, Ara-C, 5-FU, wortmannin, geldanamycin, gemcitabin or a combination thereof.

In another embodiment, provided herein are methods of treating, preventing and/or managing hematologic malignancies, which comprise administering the compounds of the present invention in combination with (e.g., before, during or after) conventional therapy including, but not limited to, surgery, immunotherapy, biological therapy, radiation therapy and other non-drug based therapy presently used to treat, prevent or manage cancer. Without being limited by theory, it is believed that the compounds of the present invention may provide additive or synergistic effects when given concurrently with such conventional therapy.

In certain embodiments, the second active agent is co-administered with the compounds of the present invention or administered with approximate 1 to 50 hour delay. In certain embodiments, the compounds of the present invention are administered first followed by administration of the second active agent with approximate 1 to 50 hour delay. In other embodiments, the second active agent is administered first followed by administration of the compounds of the present invention with approximate 1 to 50 hour delay. In some embodiments, the delay is preferably 24 hours.

In one embodiment, the compounds of the present invention can be administered in a daily amount of from about 1 to about 5000 mg alone or in combination with a second active agent disclosed herein, prior to, during, or after the use of conventional therapy.

In another embodiment, the methods provided herein comprise: a) administering to a patient in need thereof, a daily dose of about 1 mg to 5000 mg of the compounds of the present invention and b) administering a therapeutically effective amount of a second active agent such as a supportive care agent.

In one embodiment, the second agent is an alkylating agent. In another embodiment, the alkylating agent is an alkyl sulfonate and the cancer being treated is usually leukemia or lymphoma. In another embodiment, the alkyl sulfonate is busulfan. In another embodiment, the alkyl sulfonate is busulfan and the therapeutically effective amount is usually a daily dose of at least 1 mg. In another embodiment, the alkyl sulfonate is busulfan and the therapeutically effective amount is usually a daily oral dose of between about 2 mg and 8 mg. In another embodiment, the alkyl sulfonate is busulfan and the therapeutically effective amount is usually a daily oral dose of between about 1 mg and about 3 mg.

In another embodiment, the alkylating agent is a nitrogen mustard and the cancer being treated is usually bladder cancer, breast cancer, Hodgkin's disease, leukemia, lung cancer, melanoma, ovarian cancer, or testicular cancer. In another embodiment, the nitrogen mustard is chlorambucil. In another embodiment, the nitrogen mustard is chlorambucil and the therapeutically effective amount is usually at least 0.1 mg/kg. In another embodiment, the nitrogen mustard is chlorambucil and the therapeutically effective amount is usually a daily oral dose of between about 0.1 mg/kg and about 0.2 mg/kg for three to six weeks. In another embodiment, the nitrogen mustard is chlorambucil and the therapeutically effective amount is usually a dose of 0.4 mg/kg every three to four weeks. In another embodiment, the nitrogen mustard is cyclophosphamide. In another embodiment, the nitrogen mustard is cyclophosphamide and the therapeutically effective amount is usually an intravenous dose of at least 10 mg/kg. In another embodiment, the nitrogen mustard is cyclophosphamide and the therapeutically effective amount is usually an intravenous dose between about 10 mg/kg and about 15 mg/kg every seven to ten days. In another embodiment, the nitrogen mustard is cyclophosphamide and the therapeutically effective amount is usually an oral daily dose between about 1 mg/kg and about 5 mg/kg. In another embodiment, the nitrogen mustard is melphalan. In another embodiment, the nitrogen mustard is melphalan and the therapeutically effective amount is usually a daily oral dose of at least 2 mg. In another embodiment, the nitrogen mustard is melphalan and the therapeutically effective amount is usually a daily oral dose of 6 mg for two to three weeks, no melphalan for two to four weeks and then a daily oral dose of between about 2 mg and about 4 mg. In another embodiment, the nitrogen mustard is melphalan and the therapeutically effective amount is usually a daily oral dose of 10 mg/m$^2$ (body surface area) for four days every four to six weeks.

In another embodiment, the alkylating agent is a nitrosourea and the cancer being treated is usually brain tumor, colorectal cancer, Hodgkin's disease, liver cancer, lung cancer, lymphoma, or melanoma. In another embodiment, the nitrosourea is carmustine. In another embodiment, the nitrosourea is carmustine and the therapeutically effective amount is usually at least 150 mg/m$^2$. In another embodiment, the nitrosourea is carmustine and the therapeutically effective amount is usually an intravenous dose between about 150 mg/m$^2$ and 200 mg/m$^2$ every six to eight weeks.

In another embodiment, the alkylating agent is a triazene and the cancer being treated is usually Hodgkin's disease, melanoma, neuroblastoma, or soft tissue sarcoma. In another embodiment, the triazene is dacarbazine. In another embodiment, the triazene is dacarbazine and the therapeutically effective amount is usually a daily intravenous dose of between about 2.0 mg/kg and about 4.5 mg/kg for ten days every four weeks. In another embodiment, the triazene is dacarbazine and the therapeutically effective amount is usually a daily intravenous dose of 250 mg/m$^2$ for five days every three weeks. In another embodiment, the triazene is dacarbazine and the therapeutically effective amount is usually an intravenous dose of 375 mg/m$^2$ every sixteen days. In another embodiment, the triazene is dacarbazine and the therapeutically effective amount is usually an intravenous dose of 150 mg/m$^2$ for five days every four weeks.

In another embodiment, the second agent is an antineoplastic antibiotic and the cancer being treated is usually bladder cancer, breast cancer, cervical cancer, head and neck cancer, Hodgkin's disease, leukemia, multiple myeloma, neuroblastoma, ovarian cancer, sarcoma, skin cancer, testicular cancer, or thyroid cancer. In another embodiment, the antibiotic is bleomycin. In another embodiment, the antibiotic is bleomycin and the therapeutically effective amount is usually at least 10 units/m$^2$. In another embodiment, the antibiotic is bleomycin and the therapeutically effective amount is usually an intravenous, subcutaneous, or intramuscular dose of between about 10 units/m$^2$ and about 20 units/m$^2$ weekly or twice weekly. In another embodiment, the antibiotic is dactinomycin. In another embodiment, the antibiotic is dactinomycin and the therapeutically effective amount is usually at least 0.01 mg/kg. In another embodiment, the antibiotic is dactinomycin and the therapeutically effective amount is usually a daily intravenous dose of between about 0.010 mg/kg and about 0.015 mg/kg for five days every three weeks. In another embodiment, the antibiotic is dactinomycin and the therapeutically effective amount is usually an intravenous dose of 2 mg/m$^2$ every three or four weeks. In another embodiment, the antibiotic is daunorubicin. In another embodiment, the antibiotic is daunorubicin and the therapeutically effective amount is usually at least 30 mg/m$^2$. In another embodiment, the antibiotic is daunorubicin and the therapeutically effective amount is usually a daily intravenous dose of between about 30 mg/m$^2$ and about 45 mg/m$^2$ for three days. In another embodiment, the antibiotic is a liposomal preparation of daunorubicin and the therapeutically effective amount is usually an intravenous dose of 40 mg/m$^2$ every two weeks. In another embodiment, the antibiotic is doxorubicin. In another embodiment, the antibiotic is doxorubicin and the therapeutically effective amount is usually at least 15 mg/m$^2$. In another embodiment, the antibiotic is doxorubicin and the therapeutically effective amount is usually an intravenous dose of between about 60 mg/m$^2$ and about 90 mg/m$^2$ every three weeks. In another embodiment, the antibiotic is doxorubicin and the therapeutically effective amount is usually a weekly intravenous dose of between about 15 mg/m$^2$ and about 20 mg/m$^2$. In another embodiment, the antibiotic is doxorubicin and the therapeutically effective amount is usually a cycle comprising a weekly intravenous dose of 30 mg/m$^2$ for two weeks followed by two weeks of no doxorubicin.

In another embodiment, the second agent is an anti-metabolite. In another embodiment, the anti-metabolite is a folate analog and the cancer being treated is usually breast cancer, head and neck cancer, leukemia, lung cancer, non-Hodgkin's lymphoma, or osteosarcoma. In another embodiment, the folate analog is methotrexate. In another embodiment, the folate analog is methotrexate and the therapeutically effective amount is usually at least 2.5 mg. In another embodiment, the folate analog is methotrexate and the therapeutically effective amount is usually a daily oral dose of between about 2.5 mg and about 5 mg. In another embodiment, the folate analog is methotrexate and the therapeutically effective amount is usually a twice-weekly dose of between about 5 mg/m$^2$ and about 25 mg/m$^2$. In another embodiment, the folate analog is methotrexate and the therapeutically effective amount is usually a weekly intravenous dose of 50 mg/m$^2$ every two to three weeks. In another embodiment, the folate analog is pemetrexed. In another embodiment, the folate analog is pemetrexed and the therapeutically effective amount is usually at least 300 mg/m$^2$. In another embodiment, the folate analog is pemetrexed and the therapeutically effective amount is usually an intravenous dose of between about 300 mg/m$^2$ and about 600 mg/m$^2$ every two or three weeks. In another embodiment, the folate analog is pemetrexed and the therapeutically effective amount is usually an intravenous dose of 500 mg/m$^2$ every three weeks.

In another embodiment, the anti-metabolite is a purine analog and the cancer being treated is usually colorectal cancer, leukemia, or myeloma. In another embodiment, the purine analog is mercaptopurine. In another embodiment, the purine analog is mercaptopurine and the therapeutically effective amount is usually at least 1.5 mg/kg. In another embodiment, the purine analog is mercaptopurine and the therapeutically effective amount is usually a daily oral dose of between about 1.5 mg/kg and about 5 mg/kg. In another embodiment, the purine analog is thioguanidine. In another embodiment, the purine analog is thioguanidine and the therapeutically effective amount is usually at least 2 mg/kg. In another embodiment, the purine analog is thioguanidine and the therapeutically effective amount is usually a daily oral dose of between about 2 mg/kg and about 3 mg/kg.

In another embodiment, the anti-metabolite is an adenosine analog and the cancer being treated is usually leukemia or lymphoma. In another embodiment, the adenosine analog is cladribine. In another embodiment, the adenosine analog is cladribine and the therapeutically effective amount is usually at least 0.09 mg/kg. In another embodiment, the adenosine analog is cladribine and the therapeutically effective amount is usually a daily intravenous dose of 0.09 mg/kg for seven days. In another embodiment, the adenosine analog is cladribine and the therapeutically effective amount is usually a daily intravenous dose of 4 mg/m$^2$ for seven days. In another embodiment, the adenosine analog is pentostatin. In another embodiment, the adenosine analog is pentostatin and the therapeutically effective amount is usually 4 mg/m$^2$. In another embodiment, the adenosine analog is pentostatin and the therapeutically effective amount is usually an intravenous dose of 4 mg/m$^2$ every other week. In another embodiment, the adenosine analog is pentostatin and the therapeutically effective amount is usually an intravenous dose of 4 mg/m$^2$ every three weeks.

In another embodiment, the anti-metabolite is a pyrimidine analog and the cancer being treated is usually bladder cancer, breast cancer, colorectal cancer, esophageal cancer, head and neck cancer, leukemia, liver cancer, lymphoma, ovarian cancer, pancreatic cancer, skin cancer, or gastric cancer. In another embodiment, the pyrimidine analog is cytarabine. In another embodiment, the pyrimidine analog is cytarabine and the therapeutically effective amount is usually at least 100 mg/m$^2$. In another embodiment, the pyrimidine analog is cytarabine and the therapeutically effective amount is usually a daily intravenous dose of 100 mg/m$^2$ for seven days. In another embodiment, the pyrimidine analog is capecitabine. In another embodiment, the pyrimidine analog is capecitabine and the therapeutically effective amount is usually a daily dose of at least 2000 mg/m$^2$. In another embodiment, the pyrimidine analog is capecitabine and the therapeutically effective amount is usually a twice-daily oral dose of between about 1200 mg/m$^2$ and about 1300 mg/m$^2$ for 14 days. In another embodiment, the pyrimidine analog is capecitabine and the therapeutically effective amount is usually a three-week cycle wherein a twice-daily dose of about 1250 mg/m$^2$ is given for fourteen days followed by one week of rest. In another embodiment, the pyrimidine analog is fluorouracil. In another embodiment, the pyrimidine analog is fluorouracil and the therapeutically effective amount is usually at least 10 mg/kg. In another example, the pyrimidine analog is fluorouracil and the therapeutically effective amount is usually a daily intravenous dose of between about 300 mg/m$^2$ and about 500 mg/m$^2$ for at least three days. In another example, the pyrimidine analog is fluorouracil and the therapeutically effective amount is usually a daily intravenous dose of 12 mg/kg for three to five days. In another embodiment, the pyrimidine analog is fluorouracil and the therapeutically effective amount is usually a weekly intravenous dose of between about 10 mg/kg and about 15 mg/kg.

In another embodiment, the anti-metabolite is a substituted urea and the cancer being treated is usually head and neck cancer, leukemia, melanoma, or ovarian cancer. In another embodiment, the substituted urea is hydroxyurea. In another embodiment, the substituted urea is hydroxyurea and the therapeutically effective amount is usually at least 20 mg/kg. In another embodiment, the substituted urea is hydroxyurea and the therapeutically effective amount is usually an oral dose of 80 mg/kg every three days. In another embodiment, the substituted urea is hydroxyurea and the therapeutically effective amount is usually a daily oral dose of between about 20 mg/kg and about 30 mg/kg.

In another embodiment, the second agent is a platinum coordination complex and the cancer being treated is usually bladder cancer, breast cancer, cervical cancer, colon cancer, head and neck cancer, leukemia, lung cancer, lymphoma, ovarian cancer, sarcoma, testicular cancer, or uterine cancer.

In another embodiment, the platinum coordination complex is carboplatin. In another embodiment, the platinum coordination complex is carboplatin and the therapeutically effective amount is usually at least 300 mg/m². In another embodiment, the platinum coordination complex is carboplatin and the therapeutically effective amount is usually at least 300 mg/m² every four weeks. In another embodiment, the platinum coordination complex is carboplatin and the therapeutically effective amount is usually 300 mg/m² every four weeks. In another embodiment, the platinum coordination complex is carboplatin and the therapeutically effective amount is usually at least 360 mg/m² every four weeks. In another embodiment, the platinum coordination complex is cisplatin. In another embodiment, the platinum coordination complex is cisplatin and the therapeutically effective amount is usually at least 20 mg/m². In another embodiment, the platinum coordination complex is cisplatin and the therapeutically effective amount is usually a daily intravenous dose of 20 mg/m² for four to five days every three to four weeks. In another embodiment, the platinum coordination complex is cisplatin and the therapeutically effective amount is usually an intravenous dose of 50 mg/m² every three weeks. In another embodiment, the platinum coordination complex is oxaliplatin. In another embodiment, the platinum coordination complex is oxaliplatin and the therapeutically effective amount is usually at least 75 mg/m². In another embodiment, the platinum coordination complex is oxaliplatin and the therapeutically effective amount is usually between about 50 mg/m² and about 100 mg/m². In another embodiment, the platinum coordination complex is oxaliplatin and the therapeutically effective amount is usually an IV infusion of between about 50 mg/m² and about 100 mg/m² every two weeks. In another embodiment, the platinum coordination complex is oxaliplatin and the therapeutically effective amount is usually an IV infusion of between about 80 mg/m² and about 90 mg/m² every two weeks. In another embodiment, the platinum coordination complex is oxaliplatin and the therapeutically effective amount is usually a two-hour IV infusion of 85 mg/m² every two weeks.

In another embodiment, the second agent is a topoisomerase II inhibitor and the cancer being treated is usually Hodgkin's disease, leukemia, small cell lung cancer, sarcoma, or testicular cancer. In another embodiment, the topoisomerase II inhibitor is etoposide. In another embodiment, the topoisomerase II inhibitor is etoposide and the therapeutically effective amount is usually at least 35 mg/m². In another embodiment, the topoisomerase II inhibitor is etoposide and the therapeutically effective amount is usually between about 50 mg/m² and about 100 mg/m². In another embodiment, the topoisomerase II inhibitor is etoposide and the therapeutically effective amount is usually an intravenous dose of between about 35 mg/m² and about 50 mg/m² a day at least three times in five days every three or four weeks. In another embodiment, the topoisomerase II inhibitor is etoposide and the therapeutically effective amount is usually an intravenous dose of between about 50 mg/m² and about 100 mg/m² a day at least three times in five days every three or four weeks. In another embodiment, the topoisomerase II inhibitor is etoposide and the therapeutically effective amount is usually an oral dose of 100 mg/m² a day at least three times in five days every three or four weeks. In another embodiment, the topoisomerase II inhibitor is teniposide. In another embodiment, the topoisomerase II inhibitor is teniposide and the therapeutically effective amount is usually at least 20 mg/m². In another embodiment, the topoisomerase II inhibitor is teniposide and the therapeutically effective amount is usually a weekly dose of 100 mg/m². In another embodiment, the topoisomerase II inhibitor is teniposide and the therapeutically effective amount is usually a twice-weekly dose of 100 mg/m². In another embodiment, the topoisomerase II inhibitor is teniposide and the therapeutically effective amount is usually a daily dose of between about 20 mg/m² and about 60 mg/m² for five days. In another embodiment, the topoisomerase II inhibitor is teniposide and the therapeutically effective amount is usually a daily dose of between about 80 mg/m² and about 90 mg/m² for five days.

The administration mode of the compound of the present invention and a concomitant medicament are not particularly limited, provided that the compound of the present invention and the concomitant medicament are combined upon administration. Such an administration mode may for example be (1) an administration of a single formulation obtained by formulating the compound of the present invention and a concomitant medicament simultaneously, (2) a simultaneous administration via an identical route of two formulations obtained by formulating the compound of the present invention and a concomitant medicament separately, (3) a sequential and intermittent administration via an identical route of two formulations obtained by formulating the compound of the present invention and a concomitant medicament separately, (4) a simultaneous administration via different routes of two formulations obtained by formulating the compound of the present invention and a concomitant medicament separately, (5) a sequential and intermittent administration via different routes of two formulations obtained by formulating the compound of the present invention and a concomitant medicament separately (for example, the compound of the present invention followed by concomitant medicament, or inverse order) and the like.

When the compounds of the present invention are used in combination with one or more second therapeutic agents (the second active agents), the compounds may be administered either sequentially or simultaneously by any convenient route.

The combinations referred to above may conveniently be presented for use in the form of a pharmaceutical formulation and thus use of pharmaceutical formulations comprising such a combination as defined above together with a pharmaceutically acceptable carrier or excipient is a further aspect of the invention. The individual components of such combinations may be administered either sequentially or simultaneously in separate or combined pharmaceutical formulations.

When the compound of the present invention is used in combination with a second therapeutic agent active against the same disease, the dose of each compound may differ from that when the compound is used alone. Appropriate doses will be readily appreciated by those skilled in the art.

Similarly, it is clear for those skilled in the art that when the compound of the present invention is used in combination with a second therapeutic agent active against the same disease, the dose of each compound may differ from that when the compound is used alone and appropriate doses can be determined by those skilled in the art.

Preferred unit dosage formulations are those containing an effective daily dose, as herein above recited, or an appropriate fraction thereof, of the active ingredient. For example, a proposed daily dosage of compounds of the present invention may be preferably from about 1 mg to 5000 mg, and more preferably 10 mg to 500 mg per day. As described before, dosage can be changed by the individual patient, and thus not limited to these.

The subjects to be administered the compounds of this invention or pharmaceutical compositions comprising said compounds are preferably a mammalian subject including a human. The mammalian which is diagnosed with cancer is preferable among them. The mammalian which is diagnosed with cancer which PGE2 relates to is more preferable. Cancer which PGE2 relates to includes brain tumor, bone cancer, neoplasm derived from epithelial cells (epithelial cancer), for example, basal cell carcinoma, adenocarcinoma, gastroenterological cancer (e.g. lip cancer, oral cancer, esophageal cancer, intestinal cancer, colon cancer and gastric cancer), liver cancer, bladder cancer, pancreatic cancer, ovarian cancer, cervical cancer, lung cancer, breast cancer, skin cancer (e.g. squamous cell and basal cell carcinoma), prostate cancer, renal cell carcinoma, and other known cancers which affect the epithelial cells in the body. The mammalian, preferably human, which is diagnosed with at least one cancer selected from gastroenterological cancer, prostate cancer, lung cancer, and breast cancer, is more preferable.

This invention includes a method for reducing cancer cells by contacting cancer cells with the compound of the formula (I), (II), (III), or (IV) or a pharmaceutically acceptable salt thereof. The compounds of the present invention, their preferable embodiments and the like are the same as described above. The method for reducing cancer cells by contacting cancer cells with the compound of the formula (I), (II), (III), or (IV) or a pharmaceutically acceptable salt thereof is selected according to the type of cancer and the like, and typically it can be conducted by oral administration or parenteral administration of the above-described dose of the compounds represented by formula (I), (II), (III), or (IV). The second active agents may be used in the method of the present invention.

EXAMPLE

Example 1 (EP4 Receptor Selective Antagonist: Compound A: 4-((1S)-1-{[5-chloro-2-(4-fluorophenoxy)benzoyl]amino}ethyl)benzoic acid)

In the stomach of K19-Wnt1/C2mE mice (Gastroenterology Volume 131, Pages 1086-1095, 2006), tumor develops with an interaction of up-regulated Wnt signaling and induced COX-2/PGE2 pathway. Among human gastric cancer patients, Wnt up-regulation is observed in 30% to 50%, and induction of COX-2 is observed in more than 70%. Therefore, the K19-Wnt1/C2mE is positioned as a mouse model which extrapolates human gastric cancer in terms of molecular mechanism (Nature Review Cancer, Volume 7, Pages 645-658, 2007).

Figure 2:
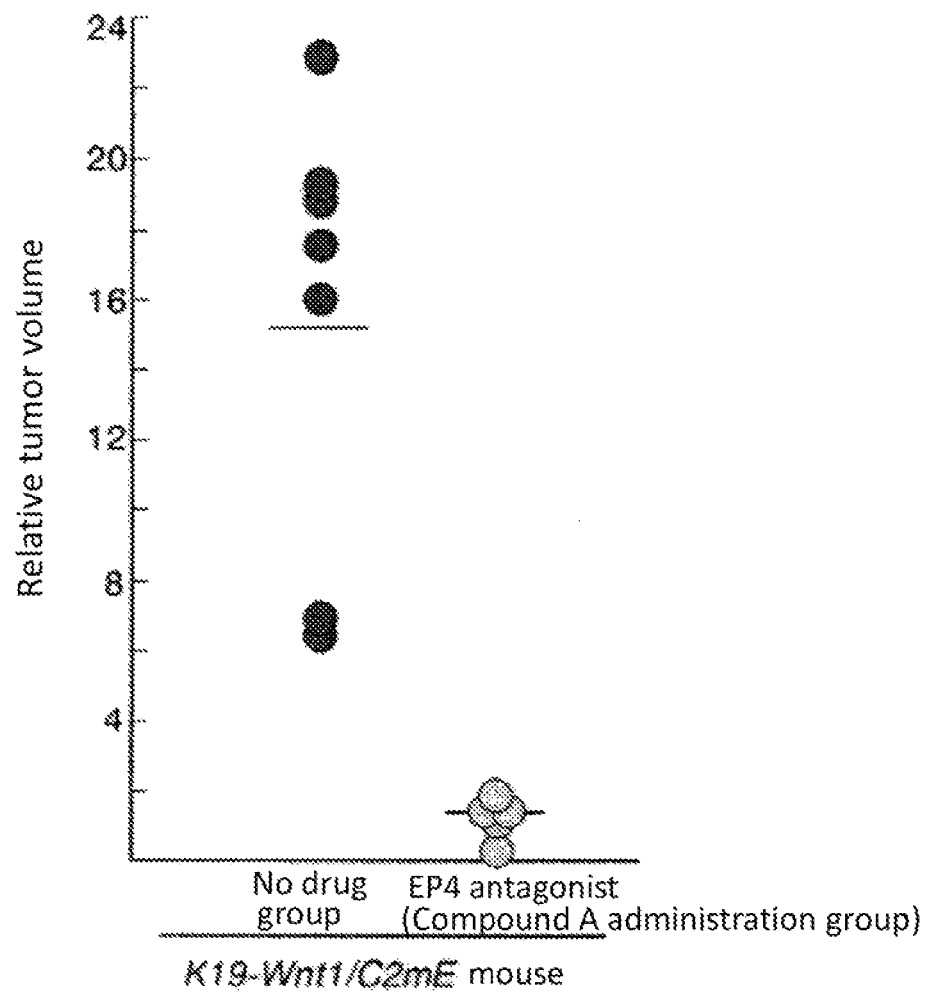
FIG. 2 shows comparison of relative gastric tumor volume between mice administered a drug and age-matched mice administered no drug.

The experiment was conducted using five spontaneous gastric cancer model mice at 50 weeks old (K19-Wnt1/C2mE mice). The mice develop large tumors in stomach at 50 weeks old, and the size of tumor can be measured with X-ray CT. The sizes of tumors were measured with X-ray CT before administration and at week 1, week 2, and week 3 after administration, and the sizes of tumors were compared. Compound A was continuously administered at a dose of 100 mg/kg twice a day for three weeks. A methyl cellulose was used as a vehicle. In two individuals in which particularly large tumor had been formed before the administration, remarkable reductions of the tumor size were observed in the first week (see FIG. 1). As shown in FIG. 1, the mean area of tumor was about 1500 to about 5000 mm$^2$ in pre-administered mice, whereas after three weeks treatment, the mean area was dramatically reduced to a range of about 300 to about 1100 mm$^2$, which clearly showed shrinkage of tumor by compound A. At three weeks post-administration, effectiveness such that tumor mass almost completely disappeared in CT images was confirmed in all the five mice which were administered the compound. As clearly shown in FIG. 2, it was confirmed that the tumor was shrunk effectively by administering compound A, compared with 55 to 60 week old K19-Wnt1/C2mE mice (n=7) which were not treated any compounds (see FIG. 2). Namely, as shown in FIG. 2, tumor was dramatically reduced by administering EP4 receptor antagonists. Further, in histological analysis of excised tissues after the treatment, disappearance of irregular glandular branching in tumor epithelium was confirmed by visual observation.

In addition, in the graph of FIG. 2, the vertical axis represents relative tumor volume, and "EP inhibitor" means the group administered compound A.

Example 2 (EP4 Receptor Selective Antagonist: Compound B: 4-[(1S)-1-{[5-chloro-2-(3-fluorophenoxy)pyridin-3-yl]carbonyl}amino)ethyl]benzoic acid)

Figure 3:
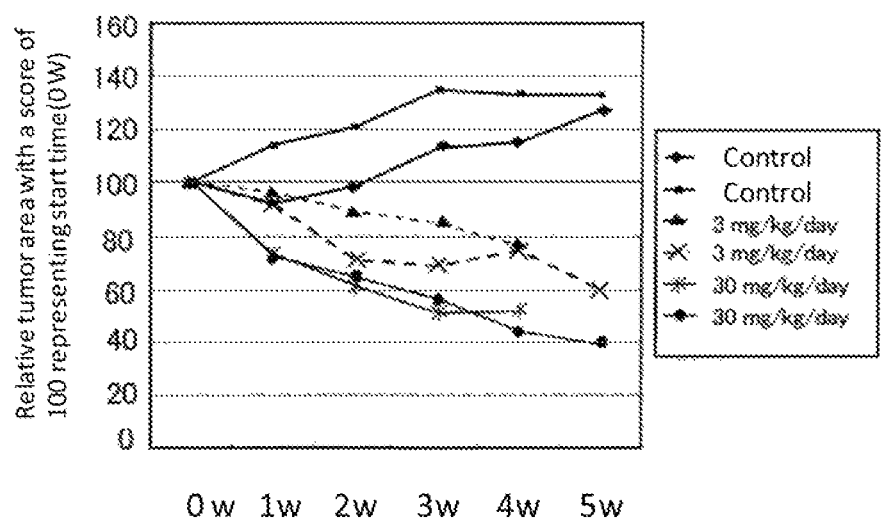
FIG. 3 shows change of mean tumor area of cross section in gastric tumor measured by X-ray CT scan.

Experiment was conducted using six gastric cancer model mice at 46 to 68 weeks old (K19-Wnt1/C2mE mice). Compound B was continuously administered per os at a dose of 3 mg/kg (n=2), 30 mg/kg (n=2) and vehicle control (n=2) once a day for five weeks. The measurements of tumor sizes were conducted in the same manner as example 1. It was confirmed by X-ray CT scanning that the sizes of tumors increased in a time-dependent manner during test period in two vehicle controls. On the other hand, it was confirmed that the sizes of tumors were reduced in a dose-dependent manner in groups administered compound B, and the effective reduction of tumor size was also observed in a group administered at a dose of 3 mg/kg (see FIG. 3). In the FIG. 3, a relative value of the mean tumor area after treatment to that before treatment (0 w) set to 100 is shown with time. Solid square (■) and solid diamond (♦) represent control model mice. Dotted triangle (▲) and dotted cross (X) represent model mice each administered compound B at a dose of 3 mg/kg. Solid star (*) and solid circle (●) represent model mice each administered compound B at a dose of 30 mg/kg. Although the size of tumor increased in a group administered vehicle, the size of tumor dramatically reduced at any dose in groups administered compound B. In addition, remarkable shrinkages of tumor lesions were also observed in autopsy, compared with a vehicle control group. Thus, it was confirmed that the size of tumor dramatically reduced in groups administered compound B, compared with that of a vehicle group.

Example 3 (Compound C: 3-[2-(4-{2-ethyl-4,6-dimethyl-1H-imidazo[4,5-c]pyridin-1-yl}phenyl)ethyl]-1-[(4-methylbenzene)sulfonyl]urea)

The experiment was conducted in the same manner as example 2 except for using compound C instead of compound B. As a result, compound C also showed the similar effects to compound B, and it was confirmed that the tumor size dramatically reduced compared with that in a group administered vehicle.

Example 4

Treatment with compound A, B, or C is performed in a xenograft animal model of human prostate cancer (a tumor-bearing mouse prepared by implantation of human prostate cancer cells to a nude mouse), and the change of tumor size is examined. In this experimental system, tumor shrinkage similar to that described above is observed in the animals treated with the compounds A, B, and C.

Example 5

Treatment with compound A, B, or C is performed in a xenograft animal model of human breast cancer (a tumor-bearing mouse prepared by implantation of human breast cancer cells to a nude mouse), and the change of tumor size is examined. In this experimental system, tumor shrinkage similar to that described above is observed in the animals treated with the compounds A, B, and C.

Example 6

Figure 4:
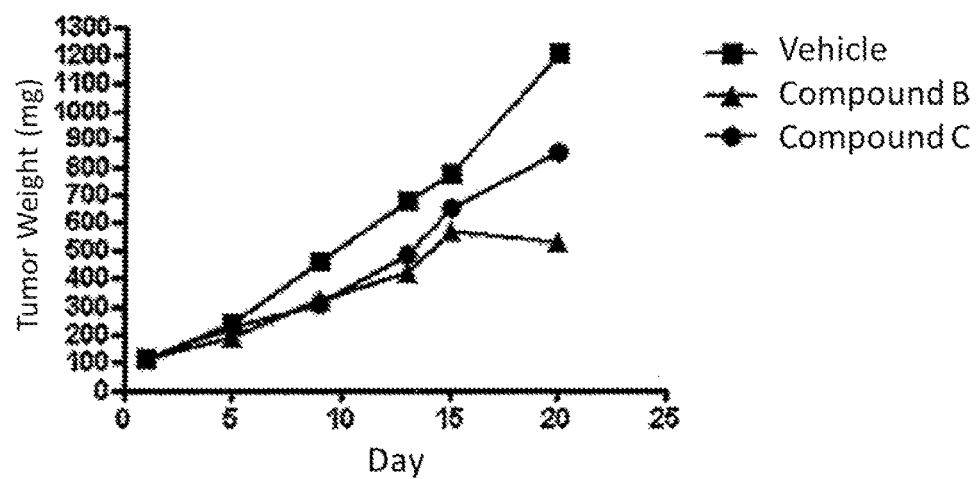
FIG. 4 shows comparison of relative colon tumor weight between mice administered a drug and age-matched mice administered no drug.

A cell line derived from mouse colon cancer, colon26, was subcutaneously implanted to CD2F1 mice. (According to the method described in Int. J. Cancer, Volume 121, Pages 878-883, 2007, this model extrapolates the colon cancer development and growth in terms of molecular mechanism.) When the mean tumor weight reached 100 mg, vehicle (n=10), compound B once a day at a dose of 30 mg/kg (n=10), or compound C twice a day at a dose of 200 mg/kg (n=10) was administered for 20 days. The tumor weight was calculated as (major axis)×(minor axis)$^2$×0.5 using the measured values. The FIG. 4 shows changes over time regarding the size of tumor in each group. In FIG. 4, solid square (■), solid triangle (▲), and solid circle (●) represent a group administered vehicle (control), a group administered compound B, and a group administered compound C, respectively. Remarkable reductions of tumor size were observed in all groups which were administered compounds compared with changes of tumor size in a vehicle group.

Example 7

In the experimental system using a xenograft animal model of human colon cancer (a tumor-bearing mouse prepared by implantation of human colon cancer cells to a nude mouse), tumor shrinkage similar to that described above is observed in the animals treated with the compounds A, B, and C.

Example 8

Figure 5:
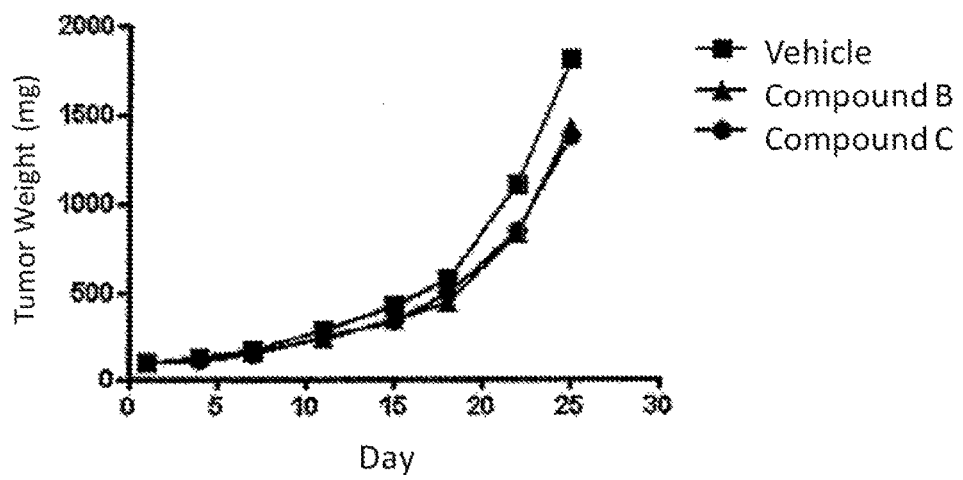
FIG. 5 shows comparison of relative lung tumor weight between mice administered a drug and age-matched mice administered no drug.

A cell line derived from mouse lung cancer, LL/2, was subcutaneously implanted to C57BL/6 mice. (According to the method described in Cancer Research. Volume 58, Pages 2583-2587, 1998, this model extrapolates the lung cancer development and growth.) When the mean tumor weight reached 100 mg, vehicle (n=10), compound B once a day at a dose of 0.3 mg/kg (n=10), or compound C twice a day at a dose of 10 mg/kg (n=10) was administered for 25 days. The tumor weight was calculated as (major axis)×(minor axis)$^2$×0.5 using the measured values. The FIG. 5 shows changes over time regarding the size of tumor in each group. In FIG. 5, solid square (■), solid triangle (▲), and solid circle (●) represent a group administered vehicle (control), a group administered compound B, and a group administered compound C, respectively. Remarkable reductions of tumor size were observed in all groups which were administered compounds compared with changes of tumor size in a vehicle group.

Example 9

In the experimental system using a xenograft animal model of human lung cancer (a tumor-bearing mouse prepared by implantation of human lung cancer cells to a nude mouse), tumor shrinkage similar to that described above is observed in the animals treated with the compounds A, B, and C.

In conclusion, the working examples regarding antitumor effect (shrinking cancer tissues) of the compounds of the present invention are described, but the present invention is not limited to these working examples. Thus, as previously mentioned, by use of the compounds of the present invention, shrinkage of cancer is observed in the cancer models which PGE2 relates to. Cancer which PGE2 relates to includes brain tumor, bone cancer, neoplasm derived from epithelial cells (epithelial cancer), for example, basal cell carcinoma, adenocarcinoma, gastroenterological cancer (e.g. lip cancer, oral cancer, esophageal cancer, intestinal cancer, colon cancer and gastric cancer), liver cancer, bladder cancer, pancreatic cancer, ovarian cancer, cervical cancer, lung cancer, breast cancer, skin cancer (e.g. squamous cell and basal cell carcinoma), prostate cancer, renal cell carcinoma, and other known cancers which affect the epithelial cells in the body.

Therefore, the therapeutic effects can be confirmed by examining the changes of the tumor size in a xenograft animal model of the above-mentioned human cancer (a tumor-bearing mouse prepared by implantation of the above-mentioned human cancer cells to a nude mouse) treated with the compounds of the present invention.

The invention claimed is:
1. A method for the treatment of colon cancer or breast cancer in which COX-2/PGE2 is expressed, which comprises administering an effective amount of a compound selected from the group consisting of:
    3-[2-(4-{2-ethyl-4,6-dimethyl-1H-imidazo[4,5-c]pyridin-1-yl}phenyl)ethyl]-1-[(4-methylbenzene)sulfonyl] urea;
    4-((1S)-1-{[5-chloro-2-(4-fluorophenoxy)benzoyl] amino}ethyl)benzoic acid; and
    4-[(1S)-1-({[5-chloro-2-(3-fluorophenoxy)pyridin-3-yl] carbonyl}amino)ethyl]-benzoic acid, or a pharmaceutically acceptable salt thereof to a human or an animal.
2. A method for reducing colon cancer tissues or breast cancer tissues in which COX-2/PGE2 is expressed, which comprises contacting the cancer tissues with a compound selected from the group consisting of:
    3-[2-(4-{2-ethyl-4,6-dimethyl-1H-imidazo[4,5-c]pyridin-1-yl}phenyl)ethyl]-1-[(4-methylbenzene)sulfonyl] urea;
    4-((1S)-1-{5-chloro-2-(4-fluorophenoxy)benzoyl] amino}ethyl)benzoic acid; and
    4-[(1S)-1-({[5-chloro-2-(3-fluorophenoxy)pyridin-3-yl] carbonyl}amino)ethyl]-benzoic acid, or a pharmaceutically acceptable salt thereof.
3. The method according to claim 1, further comprising combining the compound of 3-[2-(4-{2-ethyl-4,6-dimethyl-1H-imidazo[4,5-c]pyridin-1-yl}phenyl)ethyl]-1-(4-methylbenzene)sulfonyl]urea,
    4-((1 S)-1-{[5-chloro-2-(4-fluorophenoxy)benzoyl] amino}ethyl)benzoic acid, or
    4-[(1 S)-1-({[5-chloro-2-(3-fluorophenoxy)pyridin-3-yl] carbonyl}amino)ethyl]-benzoic acid, or the pharmaceutically acceptable salt thereof, with at least one additional active agent.

4. The method according to claim 3, wherein the additional active agent is at least one selected from the group consisting of a steroidal or nonsteroidal antiandrogen agent, an antiestrogen agent, a chemotherapeutic agent, a GnRH antagonistic peptide, an alpha-reductase inhibitor, an alpha-receptor inhibitor, an aromatase inhibitor, a 17beta-hydroxysteroid dehydrogenase inhibitor, an adrenal androgen production inhibitor, a kinase inhibitor, a drug for hormone therapy, and a drug inhibiting cell growth factor or its receptor.

5. The method according to claim 1, wherein the cancer further expresses an EP4 receptor.

6. The method according to claim 2, wherein the cancer tissues further express an EP4 receptor.

* * * * *